(12) United States Patent
Holmes et al.

(10) Patent No.: US 10,370,680 B2
(45) Date of Patent: Aug. 6, 2019

(54) METHOD OF TREATING FACTOR IX DEFICIENCY USING NUCLEASE-MEDIATED TARGETED INTEGRATION

(71) Applicant: Sangamo BioSciences, Inc., Richmond, CA (US)

(72) Inventors: Michael C. Holmes, Richmond, CA (US); Thomas Wechsler, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 80 days.

(21) Appl. No.: 14/630,128

(22) Filed: Feb. 24, 2015

(65) Prior Publication Data

US 2015/0240263 A1    Aug. 27, 2015

Related U.S. Application Data

(60) Provisional application No. 61/943,865, filed on Feb. 24, 2014.

(51) Int. Cl.
  *A01N 63/00* (2006.01)
  *C12N 15/90* (2006.01)
(52) U.S. Cl.
  CPC .. *C12N 15/907* (2013.01); *C12N 2750/14141* (2013.01)
(58) Field of Classification Search
  USPC ............. 435/325, 455; 424/93.1, 93.2, 93.21
  See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 5,976,567 A | 11/1999 | Wheeler et al. | |
| 6,007,988 A | 12/1999 | Choo | |
| 6,013,453 A | 1/2000 | Choo | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,689,558 B2 | 2/2004 | Case | |
| 6,794,136 B1 | 9/2004 | Eisenberg et al. | |
| 6,903,185 B2 | 6/2005 | Kim et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,074,596 B2 | 7/2006 | Darzynkiewicz et al. | |
| 7,153,949 B2 | 12/2006 | Kim et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,888,121 B2 | 2/2011 | Urnov et al. | |
| 7,914,796 B2 | 3/2011 | Miller et al. | |
| 7,919,313 B2 | 4/2011 | Collingwood et al. | |
| 7,951,925 B2 | 5/2011 | Ando et al. | |
| 7,972,843 B2 | 7/2011 | Hoffmann | |
| 7,972,854 B2 | 7/2011 | Miller et al. | |
| 8,034,598 B2 | 10/2011 | Miller | |
| 8,110,379 B2 | 2/2012 | DeKelver et al. | |
| 8,409,861 B2 | 4/2013 | Guschin et al. | |
| 8,586,526 B2 | 11/2013 | Gregory et al. | |
| 8,623,618 B2 | 1/2014 | Doyon et al. | |
| 8,691,966 B2 | 4/2014 | Kariko et al. | |
| 8,703,489 B2 | 4/2014 | Wang | |
| 8,772,008 B2 | 7/2014 | Doyon | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0267061 A1 | 12/2005 | Martin | |
| 2006/0063231 A1 | 3/2006 | Li et al. | |
| 2006/0188987 A1 | 8/2006 | Guschin et al. | |
| 2007/0117128 A1 | 5/2007 | Smith et al. | |
| 2007/0218528 A1 | 9/2007 | Miller | |
| 2008/0131962 A1 | 6/2008 | Miller | |
| 2008/0159996 A1 | 7/2008 | Ando et al. | |
| 2008/0188000 A1* | 8/2008 | Reik .................... C07K 14/721 435/463 |
| 2008/0299580 A1* | 12/2008 | DeKelver ............ C12N 15/907 435/6.18 |
| 2009/0068164 A1 | 4/2009 | Segal et al. | |
| 2010/0218264 A1 | 8/2010 | Cui et al. | |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Porteus (Nature Biotech., 2005, vol. 23, No. 8, p. 967-973).*
Ramirez (Unexpected failure rates for modular assembly of engineered zinc fingers. Nature Methods, 2008, 5(5): 374-375).*
Geurts (Science, Jul. 24, 2009, vol. 325, p. 433).*
Christian (Genetics, available online Jul. 26, 2008, vol. 186, p. 757-761).*
Li (Nature, Jul. 14, 2011, vol. 475, No. 7355, p. 217-221.*
High (Nature, 2005, vol. 435, p. 577 and 579).*
Cui (Clin Exp Metastasis, 2009, vol. 26, p. 849-934, abstract only on p. 883).*
Lombardo (Molecular Therapy, May 2009, vol. 17, No. Suppl. 1, p. S168).*
Papapetrou (Blood, 2010, vol. 116, Abstract 564).*

(Continued)

*Primary Examiner* — Michael C Wilson
(74) *Attorney, Agent, or Firm* — Pasternak Patent Law

(57) ABSTRACT

Disclosed herein are methods and compositions for targeted, nuclease-mediated insertion of transgene sequences into the genome of a cell.

3 Claims, 11 Drawing Sheets

(56) References Cited

U.S. PATENT DOCUMENTS

| | | |
|---|---|---|
| 2011/0027235 A1 | 2/2011 | Gregory et al. |
| 2011/0207221 A1 | 8/2011 | Cost et al. |
| 2011/0265198 A1 | 10/2011 | Gregory et al. |
| 2011/0281361 A1 | 11/2011 | DeKelver et al. |
| 2012/0017290 A1 | 1/2012 | Cui et al. |
| 2012/0128635 A1 | 5/2012 | Gregory et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2014/0080216 A1 | 3/2014 | Cost et al. |
| 2014/0093913 A1 | 4/2014 | Cost et al. |
| 2014/0155468 A1 | 6/2014 | Gregory et al. |
| 2015/0056705 A1 | 2/2015 | Conway et al. |
| 2015/0110762 A1* | 4/2015 | Holmes ............... C12N 15/907 424/93.71 |
| 2015/0159172 A1 | 6/2015 | Miller et al. |
| 2015/0166618 A1 | 6/2015 | Miller et al. |
| 2015/0174169 A1* | 6/2015 | Genovese ............. A61K 35/28 424/93.21 |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 05/111078 A2 | 11/2005 |
| WO | WO 07/014275 A2 | 2/2007 |
| WO | WO 07/030674 A2 | 3/2007 |
| WO | WO 09/042163 A2 | 4/2009 |
| WO | WO 09/054985 A1 | 4/2009 |
| WO | WO 10/079430 A1 | 7/2010 |
| WO | WO 2010/117464 * | 10/2010 |
| WO | WO 2011/011767 * | 1/2011 |
| WO | 2011078665 A1 | 6/2011 |
| WO | WO 2011/078665 * | 6/2011 |
| WO | WO 2011/097036 * | 8/2011 |
| WO | WO 2011/104382 * | 9/2011 |
| WO | WO 2012/015938 * | 2/2012 |
| WO | WO 2013/044008 * | 3/2013 |
| WO | 2013063315 A2 | 5/2013 |
| WO | 2013176772 A1 | 11/2013 |
| WO | WO 2013/176772 * | 11/2013 |
| WO | 2013192316 A1 | 12/2013 |

OTHER PUBLICATIONS

Benabdallah (Cytotherapy, 2010, 12, 394-399).*
DeKelver (Genome Res., 2010, 1133-1142).*
Hockemeyer (Nature Biotechnol., Jul. 7, 2011, vol. 29, p. 731-734).*
Wang (Circ. Res. Dec. 7, 2012, vol. 111, No. 12, p. 1494-1503).*
Anguela (Blood, Nov. 15, 2013, vol. 122, No. 21, p. 720).*
Deonarain (1998, Expert Opin. Ther. Pat., vol. 8, pp. 53-69).*
Verma (Sep. 1997, Nature, vol. 389, pp. 239-242).*
Crystal (Science, 1995, vol. 270, No. 5235, p. 404-410).*
Palu (J. Biotechnol., 1999, vol. 68, p. 1-13).*
Luo (Nature Biotechnol., 2000, vol. 18, p. 33-37).*
Pfeifer (Annu. Rev. Genomics. Hum. Genet. 2001, vol. 2, p. 177-211.*
Johnson-Saliba (Curr. Drug. Targets, 2001, vol. 2, p. 371-399).*
Shoji (Current Pharmaceutical Design, 2004, vol. 10, p. 785-796).*
Edelstein (Journal Gene Med., 2004, vol. 6, p. 597-602).*
Description of Hemophelia B, Wikipedia, 2017.*
Anderson, "Human Gene Therapy," *Science* 256(5058):808-813 (1992).
Argast, et al., "I-PPOL and I-CREL Homing Site Sequence Degeneracy Determined by Random Mutagenesis and Sequential In Vitro Enrichment," *J. Mol. Biol.* 280:345-353 (1998).
Beerli, et al., "Engineering Polydactyl Zinc-Finger Transcription Factors," *Nature Biotechnol.* 20:135-141(2002).
Belfort, et al., "Homing Endonucleases: Keeping the House in Order," *Nucleic Acids Research* 25:3379-3388 (1997).
Beurdeley, et al., "Compact Designer Talens for Efficient Genome Engineering," *Nature Communications* 4:1762 (2013) doi:10.10.38/ncomms2782.
Boch, et al., "Breaking the Code of DNA Binding Specificity of Tal-Type III Effectors," *Science* 326:1509-1512 (2009).
Boissel, et al., "MEGATALS: a Rare-Cleaving Nuclease Architecture for Therapeutic Genome Engineering," *Nucl. Acid Res.* 1-13 (2013) doi: 10.1093/nar/gkt1224.
Bonas, et al., "Genetic and Structural Characterization of the Avirulence Gene AVRBS3 From Xanthomonas Campestris PV. Vesicatoria," *Mol. Gen. Genet.* 218:127-136 (1989).
Chang, et al., "Modification IF DNA Ends Can Decrease End Joining Relative to Homologous Recombination in Mammalian Cells," *Proc. Natl. Acad. Sci. USA* 84:4959-4963.
Choo, et al., "Advances in Zinc Finger Engineering," *Curr. Opin. Struct. Biol.* 10:411-416 (2000).
Chuah, et al., "Therapeutic Factor VIII Levels and Negligible Toxicity in Mouse and Dog Models of Hemophilia A Following Gene Therapy With High-Capacity Adenoviral Vectors," *Blood* 101(5):1734-1743 (2003).
Dillon, "Regulating Gene Expression in Gene Therapy," *Tibtech* 11:167-175 (1993).
Dujon, et al., "Mobile Introns: Definition of Terms and Recommended Nomenclature," *Gene* 82:115-118 (1989).
Fraefel, et al., "Gene Transfer Into Hepatocytes Mediated by Helper Virus-Free HSV/AAV Hybrid Vectors," *Molecular Medicine* 3(12):813-825 (1997).
Gimble, et al., "Substrate Recognition and Induced DNA Distortion by the PI-SCEI Endonuclease, An Enzyme Generated by Protein Splicing," *J. Mol. Biol.* 263:163-180 (1996).
Grossman, et al., "Successful Ex Vivo Gene Therapy Directed to Liver in a Patient With Familial Hypercholesterolaemia," *Nature Genetics* 6:335-341 (1994).
Guo, et al., "Directed Evolution of an Enhanced and Highly Efficient Foki Cleavage Domain for Zinc Finger Nucleases," *J. Mol. Biol.* 400(1):96-107 (2010).
Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).
Heuer, et al., "Repeat Domain Diversity of AVRBS3-Like Genes in Ralstonia Solanacearum Strains and Association With Host Preferences in the Field," *Appl. And Envir. Micro.* 73(13):4379-4384 (2007).
Isalan, et al., "A Rapid, Generally Applicable Method to Engineer Zinc Fingers Illustrated by Targeting the HIV-1 Promoter," *Nat. Biotechnol.* 19:656-660 (2001).
Jansen, et al., "Identification of Genes That Are Associated With DNA Repeats in Prokaryotes," *Molecular Microbiology* 43(6):1565-1575 (2002).
Jasin, "Genetic Manipulation of Genomes With Rare-Cutting Endonucleases," *Trends Genet.* 12:224-228 (1996).
Kay, et al., "A Bacterial Effector Acts as a Plant Transcription Factor and Induces a Cell Size Regulator," *Science* 318:648-651 (2007).
Kremer & Perricaudet, "Adenovirus and Adeno-Associated Virus Mediated Gene Transfer," *British Medical Bulletin* 51(1):31-44 (1995).
Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted

(56) References Cited

OTHER PUBLICATIONS

Enzymatic Machinery, Functional Analogies With Eukaryotic RNAI, and Hypothetical Mechanisms of Action," *Biol. Direct 1*:7 (2006).
Matsushita, et al., "Adeno-Associated Virus Vectors Can Be Efficiently Produced Without Helper Virus," *Gene Therapy 5*:938-945 (1998).
McIntosh, et al., "Therapeutic Levels of FVIII Followng a Single Peripheral Vein Administration of RAAV Vector Encoding a Novel Human Factor VIII Variant," *Blood 121*(17):3335-3344 (2013).
Miller, "Human Gene Therapy Comes of Age," *Nature 357*:455-460 (1992).
Mitani & Caskey, "Delivering Therapeutic Genes-Matching Approach and Application," *Tibtech 11*:162-166 (1993).
Moscou, et al., "A Simple Cipher Governs DNA Recognition by TAL Effectors," *Science 326*:1501 (2009).
Nabel & Felgner, "Direct Gene Transfer for Immunotherapy and Immunization," *Tibtech 11*:211-217(1993).
Nehls, et al., "Two Genetically Separable Steps in the Differentiation of Thymic Epithelium," *Science 272*:886-889 (1996).
Olovnikov, et al., "Bacterial Argonaute Samples the Transcriptome to Identify Foreign DNA," *Mol. Cell. 51*:594-605 (2013).
Pabo, et al., "Design and Selection of Novel CYS2HIS2 Zinc Finger Proteins," *Ann. Rev. Biochem. 70*:313-340 (2001).
Perler, et al., "Protein Splicing Elements: Inteins and Exteins a Definition of Terms and Recommended Nomenclature," *Nucleic Acids Research 22*:1125-1127 (1994).
Rebar, "Development of Pro-Angiogenic Engineered Factors for the Transcription Treatment of Cardiovascular Disease," *Expert Opinion Invest. Drugs 13*(7):829-839 (2004).
Rossi, et al., "Genetic Therapies Against HIV," *Nature Biotech. 25*(12):1444-1454 (2007).
Schomack, et al., "Gene-For-Gene-Mediated Recognition of Nuclear-Targeted AVRBS3-Like Bacterial Effector Proteins," *J. Plant Physiol. 163*(3):256-272 (2006).
Segal, et al., "Custom DNA-Binding Proteins Come of Age: Polydactyl Zinc-Finger Proteins," *Curr. Opin. Biotechnol. 12*:632-637 (2001).
Sheng, et al., "Structure-Based Cleavage Mechanism of Thermus Thermophilus Argonaute DNA Guide Strand-Mediated DNA Target Cleavage," *Proc. Natl. Acad. Sci. USA 111*(2):652-657 (2013) doi: 10.1073/pnas.1321032111.
Swans, et al., "DNA-Guided DNA Interference by a Prokaryotic Argonaute," *Nature 507*(7491):258-261 (2014).
VanBrunt, "Molecular Farming: Transgenic Animals As Bioreactors," *Biotechnology 6*(10):1149-1154 (1988).
Vigne, et al., "Third-Generation Adenovectors for Gene Therapy," *Restorative Neurology and Neuroscience 8*:35-36 (1995).
Vogel, "A Bacterial Seek-And-Destroy System for Foreign DNA," *Science 344*(6187):972-973 (2014).
Yu, et al., "Progress Towards Gene Therapy for HIV Infection," *Gene Therapy 1*:13-26 (1994).
Yuan, et al., "Crystal Structure of A. Aeolicus Argonaute, A Site-Specific DNA-Guided Endoribonuclease, Provides Insights Into RISC-Mediated MRNA Cleavage," *Mol. Cell. 19*:405 (2005).

\* cited by examiner

Nucleases: mRNA
Donor: virus

Day 1:
Add AAV donor

Same Day to 48 hrs later
Add mRNA encoding nucleases

Nucleases: virus
Donor: virus

Day 1:
Add AAV nuclease

Same Day to 48 hrs later
Add AAV donor

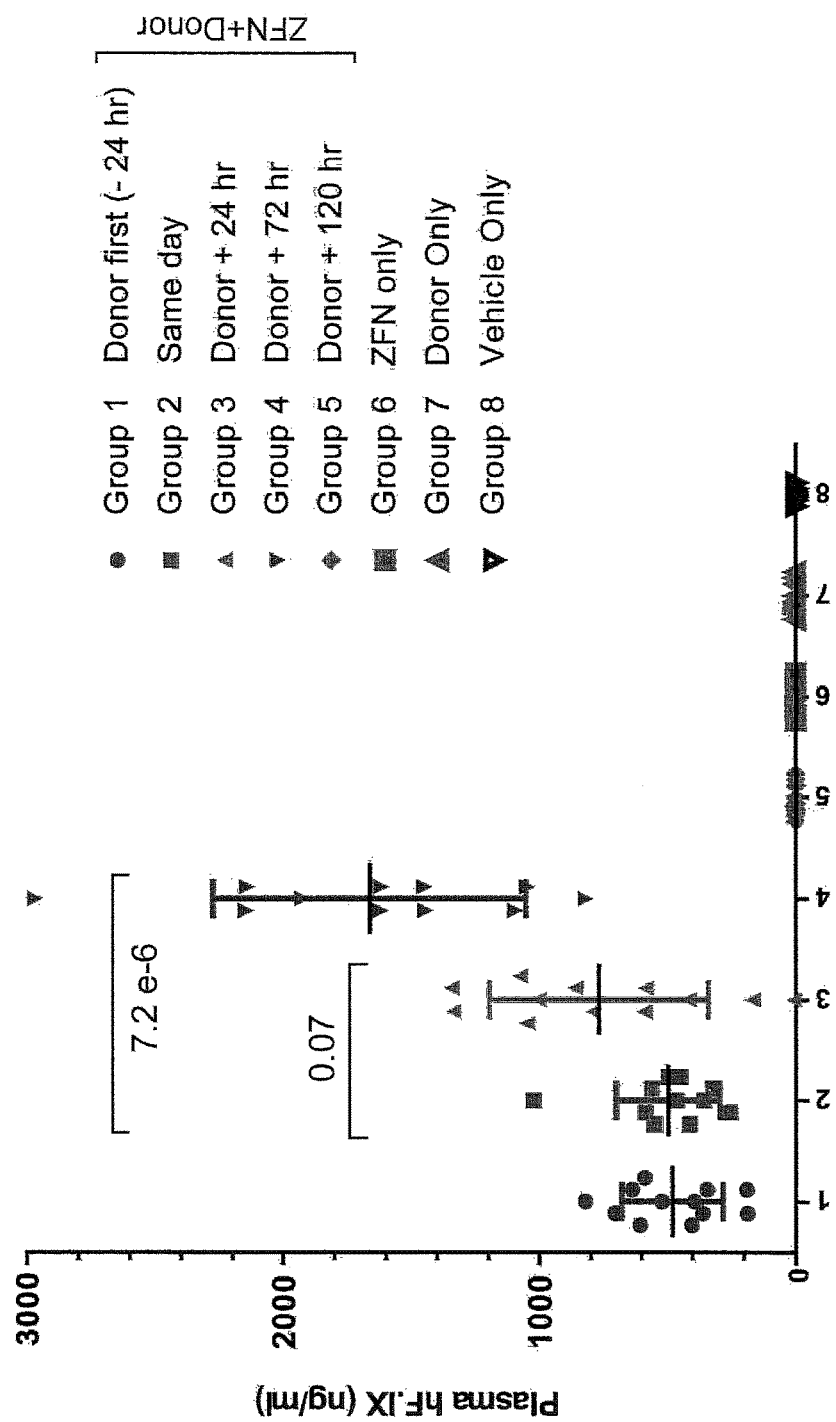

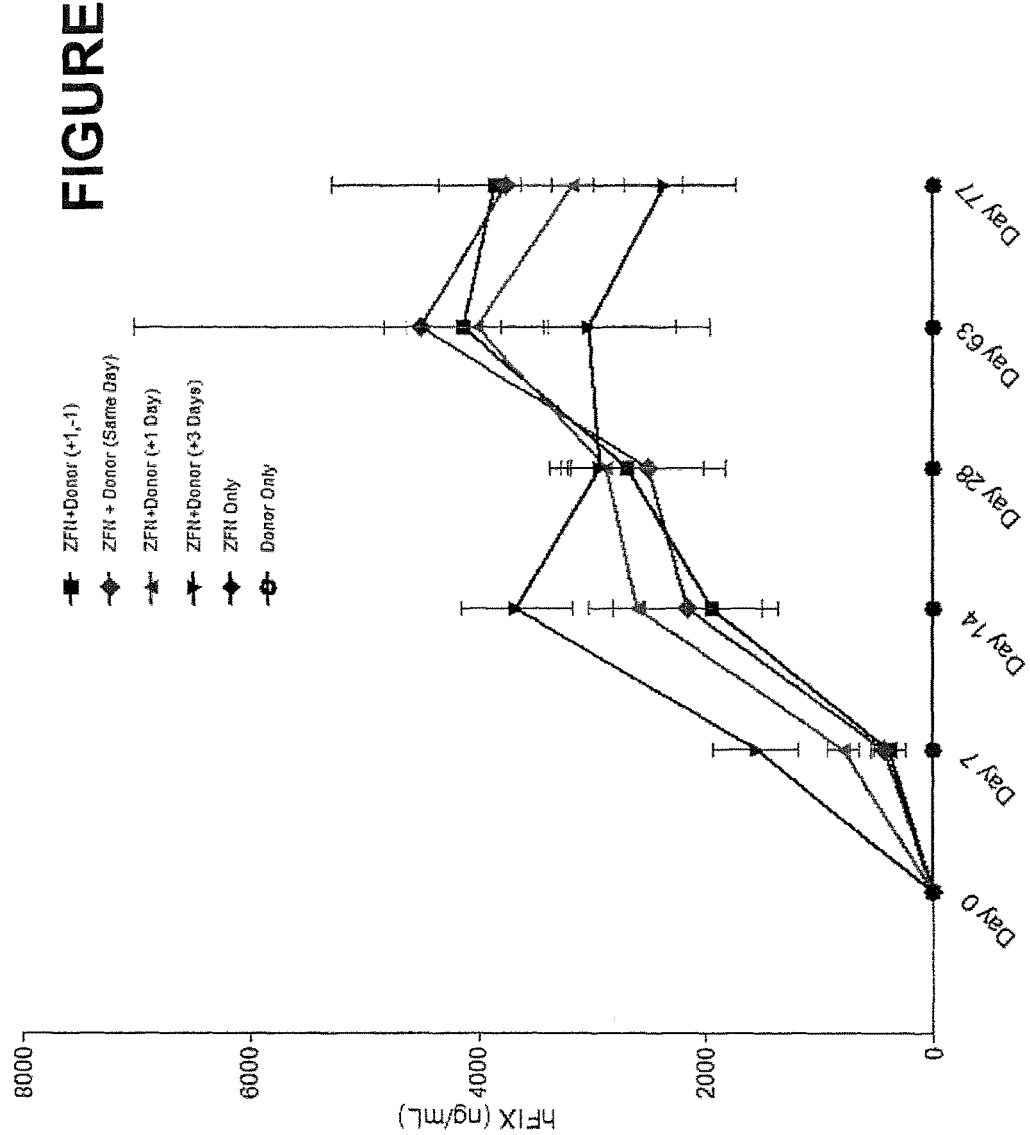

US 10,370,680 B2

METHOD OF TREATING FACTOR IX DEFICIENCY USING NUCLEASE-MEDIATED TARGETED INTEGRATION

CROSS-REFERENCE TO RELATED APPLICATIONS

The present application claims the benefit of U.S. Provisional Application No. 61/943,865, filed Feb. 24, 2014, the disclosure of which is hereby incorporated by reference in its entirety.

TECHNICAL FIELD

The present disclosure is in the fields of gene modification and increasing targeted integration of exogenous sequences into the genome of a cell.

BACKGROUND

Engineered nucleases, including zinc finger nucleases, TALENs, CRISPR/Cas nuclease systems, Ttago nucleases and homing endonucleases designed to specifically bind to target DNA sites are useful in genome engineering. For example, zinc finger nucleases (ZFNs) and TALENs (including TALENs comprising Fok1-TALE DNA binding domain fusions, Mega TALs and cTALENs) are proteins comprising engineered site-specific zinc fingers or TAL-effector domains fused to a nuclease domain. Such nucleases have been successfully used for genome modification in a variety of different species at a variety of genomic locations. See, for example, See, e.g., U.S. Pat. Nos. 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983, 20130177960 and 20150056705, the disclosures of which are incorporated by reference in their entireties for all purposes.

Cleavage of a target nucleotide sequence by these nucleases increases the frequency of homologous recombination (HR) with a donor at the targeted locus by more than 1000-fold. Homology-directed repair (HDR) of a nuclease-mediated cleavage event can be used to facilitate targeted insertion of a gene (transgene) by co-delivering a donor molecule encoding a gene flanked by sequence homologous to region surrounding the break site. In addition, the repair of a site-specific DSB by non-homologous end joining (NHEJ) can also result in gene modification, including gene (transgene) insertion by NHEJ-dependent end capture. See, e.g., U.S. Patent Publication No. 20110207221. In addition to targeted integration of a transgene, nuclease-mediated cleavage and repair by NHEJ can result in non-specific insertions and/or deletions ("indels") at the site of the break. Thus, nucleases specific for the targeted region can be utilized such that the transgene construct is inserted by either HDR- or NHEJ-driven processes, or for knockout of a gene through error-prone NHEJ repair of the nuclease-mediated DSB. Gene correction may also be accomplished using targeted nucleases and donor molecules designed to replace a specified region in an endogenous gene with sequences supplied in the donor. A specific double strand break (DSB) is introduced in the gene and in the presence of the gene correcting donor DNA, the sequences of interest are replaced using those of the donor via homology dependent recombination.

This nuclease-mediated targeted transgene insertion approach offers the prospect of improved transgene expression, increased safety and expressional durability, as compared to classic integration approaches, since it allows exact transgene positioning to minimize the risk of gene silencing or activation of nearby oncogenes. However, efficiency of nuclease activity can be influenced by a variety of factors such as accessibility of the chromosomal DNA target and the quality of the binding interaction between the nuclease and its target nucleic acid. Efficiency of these approaches in vivo is further complicated by factors such as target tissue accessibility and tissue uptake of vectors that deliver the nucleases and transgene donors, and nuclease expression levels that can be achieved in vivo. To increase the success rate of nuclease driven genomic modifications, researchers often have to resort to introducing selectable markers during donor integration in order to be able to select variants that have had modifications from those that have not been modified (see, for example, U.S. Pat. No. 6,528,313). For a number of applications, use of selectable markers is not desirable as this technique leaves an additional gene or nucleic acid sequence inserted into the genome.

Thus, there remains a need for compositions and methods for increasing nuclease-mediated targeted integration of transgenes to allow for even more efficient use of these powerful tools.

SUMMARY

Disclosed herein are methods and compositions for nuclease-mediated integration of one or more exogenous sequences into a target sequence via sequential administration of the nuclease(s) and the exogenous sequences(s). The methods and compositions described herein increase the efficiency of nuclease-mediated targeted integration of exogenous sequences (transgenes). In particular, the methods and compositions involve sequential separate administration of nucleases and transgenes, for example, administration of separate solutions of nuclease(s) and transgene(s) with a delay between the separate administrations. The delay between administrations may be minutes, hours or days or even longer, for example, 10 minutes or more, 30 minutes or more, 1 hour or more, 2 hours or more, 3 hours or more, 24 hours or more, 36 hours or more, 48 hours or more, 72 hours or more, or 4 days or more, 5 days or more, 6 days or more, a week or more, or even longer between administrations. The methods and compositions described herein result in an enhanced efficiency of transgene integration (e.g., an increase of 10%, 20%, 30%, 40%, 50%, 60%, 70%, 80%, 90%, 100%, 1.5-fold, 2-fold, 3-fold, 4-fold, 5-fold, 6-fold, 7-fold, 8-fold, 9-fold, 10 to 100 fold (or any value therebetween) or even more in transgene integration) as compared to transgenes integrated using alternate methods (e.g., concurrent administration or serial administrations less than at least 4 hours apart).

Thus, in one aspect, described herein is a method of integrating an exogenous sequence into a target sequence of an isolated cell, the method comprising sequentially administering (i) one or more nucleases that cleave the target sequence and (ii) one or more donor sequences that are integrated into the target sequence following cleavage of the target sequence by the one or more nucleases, wherein there is a delay of at least 24 hours between the sequential administration. In certain embodiments, the delay between the sequential administrations is between 24 and 72 hours. In one embodiment, the one or more nucleases are administered prior to the one or more donors and the one or more nucleases and/or one or more donors are administered using a plasmid, a viral vector (e.g., AAV vector) or in RNA, mini-circle or linear DNA form. In another embodiments, the one or more donors are administered prior to the one or more nucleases and the one or more nucleases are administered in RNA form (e.g., in mRNA form).

Nucleases, for example engineered meganucleases, zinc finger nucleases (ZFNs), TALE-nucleases (TALENs including fusions of TALE effectors domains with nuclease domains from restriction endonucleases and/or from meganucleases (such as mega TALEs and compact TALENs)) Ttago nucleases and/or CRISPR/Cas nuclease systems are used to cleave DNA at an endogenous locus (e.g. safe harbor gene or locus of interest) in the cell into which any exogenous donor sequence (transgene) is inserted. Targeted insertion of a donor transgene may be via homology directed repair (HDR) or non-homology repair mechanisms (e.g., NHEJ-mediated end capture). Insertions and/or deletions ("indels") of nucleotides (e.g., endogenous sequences) may also occur at the site of integration. The nuclease can induce a double-stranded (DSB) or single-stranded break (nick) in the target DNA. In some embodiments, two nickases are used to create a DSB by introducing two nicks. In some cases, the nickase is a ZFN, while in others, the nickase is a TALEN or a CRISPR/Cas system.

In one aspect, the methods comprise administering one or more nucleases to a cell (e.g., one or more vectors encoding the nucleases) such that the vectors comprising the encoded nucleases are taken up by the cell, then the nucleases cleave a specified endogenous locus of the cell's genome and finally, after a period of time, administering one or more exogenous (donor) sequences to the cells (e.g. one or more vectors comprising these exogenous sequences) such that the exogenous sequences are integrated (in a targeted manner) at or near the cleaved genome (e.g., the nuclease(s) binding and/or cleavage site(s)), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s). The exogenous sequence may be administered any time after administration of the nucleases, for example, anywhere from 10 minutes or more, 30 minutes or more, 1 to 72 hours or more (4 days, 5 days, 6 days, 7 days or more). In certain embodiments, the period of time between administration of the nuclease(s) and donor is between 24 hours and 4 days, preferably 48-72 hours. In certain embodiments, the cell is an isolated cell and is cultured between administration of the nuclease(s) and administration of the donor transgene.

In another aspect, the methods comprise administration of an exogenous sequence (e.g. a vector, plasmid, mini-circle or linear DNA comprising the exogenous sequences) to a cell followed by administration of the nuclease (e.g. administration of an mRNA encoding the nuclease, vector or plasmid encoding the nuclease, or administration of the nuclease as its protein form). For example, the mRNA encoding the nuclease, or the protein nuclease may be administered any time after the exogenous sequence, for example, anywhere from 10 minutes or more, 30 minutes or more, 1 to 72 hours or more (4 days, 5 days, 6 days, 7 days or more). In certain embodiments, the period of time between administration of the donor and the nuclease(s) is between 24 hours and 4 days, preferably 48-72 hours.

In some embodiments the nuclease(s) is/are administered as an RNA (e.g., as their encoding mRNAs). In some embodiments, the mRNA comprises the two nucleases of a nuclease pair, separated by a ribosomal stuttering site, and internal ribosome entry site or the like (e.g. a 2A sequence or IRES). In other embodiments, two mRNAs encoding the two nucleases in a nuclease pair are separate mRNAs which can be combined before or during administration to the cell. In some embodiments, the mRNAs are modified or capped.

Cleavage can occur through the use of specific nucleases such as engineered zinc finger nucleases (ZFNs), transcription-activator like effector nucleases (TALENs), using Ttago nucleases or using the CRISPR/Cas system with an engineered crRNA/tracr RNA ('single guide RNA') to guide specific cleavage. In some embodiments, two nickases are used to create a DSB by introducing two nicks. In some cases, the nickase is a ZFN, while in others, the nickase is a TALEN or a CRISPR/Cas system. Targeted integration of exogenous donor sequences may occur via homology directed repair mechanisms (HDR) and/or via non-homology repair mechanisms (e.g., NHEJ-mediated end capture). The nucleases as described herein may bind to and/or cleave the region of interest in a coding or non-coding region within or adjacent to the gene, such as, for example, a leader sequence, a regulatory sequence, trailer sequence or intron, or within a non-transcribed region, either upstream or downstream of the coding region. In certain embodiments, the nuclease cleaves the target sequence at or near the binding site.

In any of the methods described herein, the donor sequence may comprise one or more transgenes that express protein products. In certain embodiments, the protein products are therapeutic in that they are functional versions of proteins aberrantly expressed in a disorder (e.g., a genetic disorder such as a hemophilia, lysosomal storage diseases, metabolic diseases, hemoglobinopathies and the like). In certain embodiments, the transgene encodes one or more functional clotting factor proteins (e.g., Factor VII, Factor VIII Factor IX and/or Factor X). In some embodiments, the donor sequence is designed to correct a mutation in an endogenous gene via nuclease-dependent HDR.

The nuclease may target any endogenous locus. In certain embodiments, the transgene is integrated in a site-specific (targeted) manner using at least one nuclease (e.g., ZFNs, TALENs and/or CRISPR/Cas systems) specific for a safe harbor locus (e.g. CCR5,HPRT, AAVS1, Rosa or albumin. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983, 20130122591, 20130177960 and 20150056705).

In another aspect, described herein is a method of genetically modifying a cell to comprise an exogenous sequence, the method comprising cleaving an endogenous gene in the cell using one or more nucleases (e.g., ZFNs, TALENs, CRISPR/Cas) and, after a period of time, administering the transgene to the cell such that it is integrated into the endogenous locus and expressed in the cell. In certain embodiments, the endogenous gene is a safe harbor gene such as CCR5, HPRT, AAVS1, Rosa or albumin locus.

In another aspect, described herein is a method of genetically modifying a cell to comprise one or more exogenous sequences, the method comprising administering a vector comprising the exogenous sequence to the cell, allowing sufficient time for uptake of the vector comprising the exogenous sequence by the cell, and then administration of mRNAs encoding one or more nucleases (e.g. ZFNs, TAL-ENs (TAL-effector domains and nuclease domains (restriction endonucleases and/or meganuclease)) and/or a CRISPR/Cas system) or administering nucleases as proteins, such that the nucleases cleave the endogenous gene and the exogenous sequences are integrated and expressed. In certain embodiments, the endogenous locus is a safe harbor locus such as CCR5, HPRT, AAVS1, Rosa or albumin gene.

In another aspect, provided herein are methods for providing a functional protein lacking or deficient in a patient, for example for treating genetic disorders. In certain embodiments, the methods comprise integrating a sequence encoding the functional protein in a cell in a subject in need thereof using the ordered sequential administration of nuclease(s) and transgene(s) as disclosed herein. In other embodiments, the methods comprise administering a genetically modified cell (expressing a functional version of one or more proteins aberrantly expressed in a subject) directly to the subject. Thus, an isolated cell may be introduced into the subject (ex vivo cell therapy) or a cell may be modified when it is part of the subject (in vivo). Also provided is the use of the donors and/or nucleases described herein for the treatment of a disorder, for example, in the preparation of medicament for treatment of a genetic disorder. In certain embodiments, the exogenous sequence is delivered using a viral vector, a non-viral vector (e.g., plasmid) and/or combinations thereof.

In any of the compositions and methods described, the nuclease(s) and/or transgene(s) may be carried on an AAV vector, including but not limited to AAV1, AAV3, AAV4, AAV5, AAV6, AAV8, AAV9 and AAVrh10 or pseudotyped AAV such as AAV2/8, AAV8.2, AAV2/5 and AAV2/6 and the like. In certain embodiments, the nucleases and transgene donors are delivered using the same AAV vector types. In other embodiments, the nucleases and transgene donors are delivered using different AAV vector types. The nucleases and transgenes may be delivered using two or more vectors, for example, two vectors where one carries the nuclease(s) (e.g., left and right ZFNs of a ZFN pair, for example with a 2A peptide) and one carries the transgene; or three vectors where one vector carries one nuclease of a nuclease pair (e.g., left ZFN), a separate vector carries the other nuclease of a nuclease pair (e.g., right ZFN) and a third separate vector carries the transgene. In embodiments, in which two or more vectors or used, the vectors may be used at the same concentrations or in different ratios, for example, the nuclease vector(s) may be administered at 2-fold, 3-fold, 4-fold, 5-fold or more higher concentrations than the transgene vector(s).

In any of the compositions and methods described herein, the nuclease(s) may be delivered as mRNAs encoding said nucleases. In some embodiments, a single mRNA encoding the two nucleases of a nuclease pair wherein the coding sequences for each nuclease are separated by a 'self-cleaving' sequence (e.g., a 2A sequence) is described. In other embodiments, each nuclease of a nuclease pair is comprised as a single mRNA, wherein two single mRNAs are used together to administer a nuclease pair. In any of the mRNA compositions described herein, the mRNA may be modified to increase stability and/or efficiency of transcription, or may include modified nucleosides (for examples, see U.S. Pat. Nos. 8,691,966 and 7,074,596), or the mRNA may be delivered via a formulated particle or as an encapsulated liposome (see, e.g. U.S. Pat. No. 5,976,567).

In any of the compositions and methods described herein, the transgene may encode a protein, for example a functional version of a protein lacking and/or aberrantly expressed in a disorder. In some embodiments, the transgene may encode a non-naturally occurring protein with enhanced characteristics as compared to its naturally occurring counterpart. In any of the compositions or methods described herein, the transgene also comprises a transcriptional regulator while in others, it does not and transcription is regulated by an endogenous regulator. In another aspect, the methods of the invention comprise a composition for therapeutic treatment of a subject in need thereof. In some embodiments, the composition comprises engineered stem cells comprising a safe harbor specific nuclease, and a transgene donor. In other embodiments, the composition comprises engineered virus particles comprising transgene donors and specific nucleases and/or modified mRNAs for performing in vivo gene modification.

In any of the compositions or methods described herein, the cell may be a eukaryotic cell. Non-limiting examples of suitable cells include eukaryotic cells or cell lines such as secretory cells (e.g., liver cells, mucosal cells, salivary gland cells, pituitary cells, etc.), blood cells (red blood cells), red blood precursory cells, hepatic cells, muscle cells, stem cells (e.g., embryonic stem cells, induced pluripotent stem cells, hepatic stem cells, hematopoietic stem cells (e.g., CD34+)) or endothelial cells (e.g., vascular, glomerular, and tubular endothelial cells). Thus, the target cells may be human cells, or cells of other mammals (including veterinary animals), especially nonhuman primates (*Macaca mulatta*: rhesus macaque, *Macaca fascicularis*: cynomolous monkey) and mammals of the orders *Rodenta* (mice, rats, hamsters), *Lagomorpha* (rabbits), *Carnivora* (cats, dogs), and *Arteriodactyla* (cows, pigs, sheep, goats, horses). In some aspects, the target cells comprise a tissue (e.g. liver). In some aspects, the target cell is a stem cell (e.g., an embryonic stem cell, an induced pluripotent stem cell, a hepatic stem cell, etc.) or animal embryo by any of the methods described herein, and then the embryo is implanted such that a live animal is born. The animal is then raised to sexual maturity and allowed to produce offspring wherein at least some of the offspring comprise the genomic modification. The cell can also comprise an embryo cell, for example, of a mouse, rat, rabbit or other mammalian cell embryo. The cell may be from any organism, for example human, non-human primate, mouse, rat, rabbit, cat, dog or other mammalian cells. The cell may be isolated or may be part of an organism (e.g., subject).

In any of the methods and compositions described herein, the transgene may be integrated into the endogenous safe harbor gene such that some, all or none of the endogenous gene is expressed, for example a fusion protein with the integrated transgene. In some embodiments, the endogenous safe harbor gene is an albumin gene and the endogenous sequences are albumin sequences. The endogenous sequences may be present on the amino (N)-terminal portion of the exogenous protein and/or on the carboxy (C)-terminal portion of the exogenous protein. The albumin sequences may include full-length wild-type or mutant albumin sequences or, alternatively, may include partial albumin amino acid sequences. In certain embodiments, the albumin sequences (full-length or partial) serve to increase the serum half-life of the polypeptide expressed by the transgene to which it is fused and/or as a carrier. In other embodiments, the transgene comprises albumin sequences and is targeted for insertion into another safe harbor within a genome. Furthermore, the transgene may include an exogenous promoter (e.g., constitutive or inducible promoter) that drives its expression or its expression may be driven by endogenous control sequences (e.g., endogenous albumin promoter). In some embodiments, the donor includes additional modifications, including but not limited to codon optimization, addition of glycosylation sites, signal sequences and the like.

Furthermore, any of the methods described herein may further comprise additional steps, including cold-shocking of the cells at any time (U.S. Pat. No. 8,772,008), partial hepatectomy or treatment with secondary agents that enhance transduction and/or induce hepatic cells to undergo cell cycling. Examples of secondary agents include gamma irradiation, UV irradiation, tritiated nucleotides such as thymidine, cis-platinum, etoposide, hydroxyurea, aphidicolin, prednisolone, carbon tetrachloride and/or adenovirus.

The methods described herein can be practiced in vitro, ex vivo or in vivo. In certain embodiments, the methods are performed in (and/or compositions such as modified cells delivered to) a live, intact mammal. The mammal may be at any stage of development at the time of delivery, e.g., embryonic, fetal, neonatal, infantile, juvenile or adult. Additionally, targeted cells may be healthy or diseased. In certain embodiments, one or more of the compositions are delivered intravenously (e.g., to the liver via the hepatic portal vein, for example tail vein injection), intra-arterially, intraperitoneally, intramuscularly, into liver parenchyma (e.g., via injection), into the hepatic artery (e.g., via injection), and/or through the biliary tree (e.g., via injection).

For targeting the compositions to a particular type of cell, e.g., platelets, fibroblasts, hepatocytes, hematopoietic stem/progenitor cells etc., one or more of the administered compositions may be associated with a homing agent that binds specifically to a surface receptor of the cell. For example, the vector may be conjugated to a ligand (e.g., galactose) for which certain hepatic system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

A kit, comprising the compositions (e.g., genetically modified cells, ZFPs, CRISPR/Cas system and/or TALEs of the invention, is also provided. The kit may comprise nucleic acids encoding the nucleases, (e.g. RNA molecules or nuclease-encoding genes contained in a suitable expression vector or proteins), donor molecules, suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 1A shows the method if the nuclease(s) is delivered as mRNA. In this case, the donor containing AAV virus is delivered to the cell, followed by delivery of the nuclease-encoding mRNA up to 48 hours after delivery of the donor. FIG. 1B shows the method if both donor and nuclease are delivered via AAV viruses. In this instance, the nuclease-containing virus is delivered first, taken up by the cells, and then the donor-containing virus is delivered up to 48 hours after delivery of the nuclease virus.

FIG. 3A is a schematic showing the insertion of the human F9 gene into the albumin locus in non-human primate (NHP) primary hepatocytes. The picture illustrates that the hF9 gene donor was flanked by NHP (rhesus) albumin homology arms. FIG. 3B shows the initial translation product from the transgene insertion, and shows the proteolytic cleavage sites on the prepro hF.IX peptide. FIG. 3C shows the expression of hF.IX detected in the cell supernatant. This graph shows the results using two NHP(rhesus) albumin specific ZFN pairs, 36806/35396 and 37804/43043 where the mRNAs encoding the ZFNs were added either 24 or 48 hours following addition of the AAV-containing hF9 transgene. The highest expression levels in this experiment were obtained when the mRNAs encoding the ZFNs were added 24 hours after the transgene containing AAV.

FIG. 5A depicts a graph showing the results of a hFIX specific ELISA assay when the AAV particles were delivered at a ratio of donor AAV: ZFN1 AAV: ZFN2 AAV of 10:1:1, while FIG. 5B depicts a graph showing the results when the ratios were varied (donor AAV: ZFN1 AAV: ZFN2 AAV of 3:1:1; 10:1:1 or 16:1:1). Both graphs show that the optimum hF.IX transgene expression was found when the donor-AAV transgene virus was added 24 hours after the ZFN-AAV and that under these conditions a lower Donor: ZFN ratio is beneficial.

FIG. 7A depicts a characterization of the ZFN activity at days 4 and 8 post transfection through an analysis of the percent of insertions and deletions ("indels") detected at the albumin cleavage site by the ZFNs under the varying ZFN:donor virus ratio conditions. This data shows that ZFN activity decreases when higher amounts of donor virus are introduced on the same day. In contrast, when donor addition was delayed 24 hours, the negative impact the donor vector had on ZFN activity was no longer apparent even at a high donor:ZFN ratios. The data depicted in the day 8 samples is from duplicate samples. FIG. 7B depicts the amount of hF9 transgene expression in the same conditions as described in FIG. 7A. hF.IX expression is highest when the AAV-donor vector is introduced to the culture 24 hours after the AAV-ZFN.

FIG. 8 depicts expression of an hF9 transgene in C57/B16 mice under various donor and ZFN virus delay protocols. The virus used was AAV2/8 at a 6:1:1 ratio of donor-AAV: ZFN1-AAV: ZFN2-AAV virus. The conditions were as follows: Donor added first, ZFN virus added 24 hours later (circles), administration of both virus at the same time (squares), administration of ZFN virus first, followed by donor virus 24 hours later (triangles), administration of ZFN virus first, followed by donor virus 72 hours later (inverted triangles), administration of ZFN virus first, followed by donor virus 120 hours later (diamonds). Control groups include ZFN only, Donor only and Vehicle only. P-values represent student's T-test results between group 2 and 3 or groups 2 and 4, respectively.

FIG. 9A depicts the ZFN cleavage activity as measured by the percent of indels detected (as described above) at the albumin locus in liver genomic DNA from all groups. FIG. 9B depicts ZFN expression via Western blot analysis in the same liver tissues. ZFN activity and expression was highest when the ZFN-containing AAV was added either alone or 3 days prior to the addition of the donor-containing AAV.

FIG. 10 is a graph showing levels of hF.IX in mouse serum following infection with the AAV-ZFN and AAV-donor virus. AAV-donor was given to the mice either one day before the AAV-ZFN virus, given the same day, or given 1 or 3 days after the AAV-ZFN. hF.IX was detected using ELISA following serial bleeds of the different cohorts.

FIG. 11A is a graph depicting hF.IX levels in Rhesus plasma from 8 treated animals (Day 0 to Day 28) as determined by ELISA. AAV-donor was given to the monkeys either on the same day, or given 1 or 2 days after the AAV-ZFN. FIG. 11B shows the peak hF.IX levels from the same study achieved during the whole study duration.

DETAILED DESCRIPTION

Disclosed herein are compositions and methods for integrating one more exogenous donor sequences into a target site of a cell. The methods and compositions involve sequential administration of (i) one or more nucleases that cleave the target sequence and (ii) one or more donor sequences that are integrated into the target sequence following cleavage of the target sequence by the nuclease and in which there is a delay of minutes, hours or days between the administration of the nuclease(s) and the exogenous sequence(s). The methods and compositions described herein increase the efficiency of targeted gene correction or integration of an exogenous sequence into an endogenous genomic locus using a targeted nuclease by adhering to specific methodologies of sequential administration of the nuclease(s) and donor construct, where the order of the sequence is dependent upon the form used for delivery of the nucleases and donor.

Figure 1A:
FIGS. 1A and 1B depict schemes for varying the order of addition of donor and nuclease, depending on whether both are to be delivered in viral vectors or if the nuclease is delivered as mRNA.
Figure 1B:
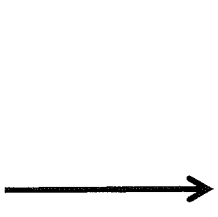

In particular, administration of the donor transgene (e.g., protein encoding sequence or DNA sequence encoding a RNA such as an shRNA), after administration of the nuclease(s) when both nucleases and donor are supplied as viral particles results in increased transgene integration as compared to methods in which the donor and nucleases are administered together (concurrently) or with a shorter or longer delay. The donor transgene may be administered from minutes to hours to days after the nuclease(s), for example, 8 to 72 hours (or any time therebetween) or 4 days, 5 days, 6 days or even more. Alternatively, when the nuclease is administered as mRNA(s), it is preferred to administer the viral particle comprising the donor transgene first, allow for sufficient time for uptake by the target cell, and then treat with the nuclease encoding mRNAs. The nuclease encoding mRNAs may be administered from minutes to hours to days after the donor(s), for example, 8 to 72 hours (or any time therebetween) or 4 days, 5 days, 6 days or even more. In either scenario, the cell is given sufficient time for viral uptake. Without being bound by any particular theory, when both the nucleases and transgene donor are administered via virus, it is possible that the two types of particles compete for the same uptake receptors and diminish overall activity. Another possible mode of competition between the viruses is after they enter the cell. Both ZFN and Donor virus have to first escape the endosomes in order to enter the nucleus. The resulting free single-stranded AAV genome then has to be converted into a double-stranded form to a) either serve as Donor or b) to be transcribed and produced the ZFN protein. Any of these steps could be rate-limiting and could therefore be sensitive towards AAV competition. It is also beneficial that if sufficient time between the administration of the two particle types is allowed, the nuclease virus will have been taken up and the nucleases will have started acting to create the specific DSB at the endogenous genomic target before the transgene donor virus is introduced. When the nuclease is supplied as mRNA, competition for uptake receptors is not an issue as the mRNA is taken up immediately during the transfection procedure (see FIG. 1). In some specific cell types (e.g. CD34+ hematopoietic stem cells, it may be preferable to treat the cells with the donor-AAV immediately following nuclease introduction via mRNA.

An exogenous sequence can encode any protein or peptide involved in hemophilia, for example F8, F.IX and/or functional fragments thereof. Also disclosed are methods of treating a hemophilia using a cell as described herein and/or by modifying a cell (ex vivo or in vivo) as described herein.

The transgene may encode a protein product, for example a functional version of a protein that is lacking, aberrantly expressed and/or non-functional in the cell, for example a protein lacking in a subject with hemophilia (e.g., Factor VII, F8, F.IX, Factor X, and/or functional fragments thereof), a protein lacking in a subject with a lysosomal storage disease, a protein lacking in a subject with a hemoglobinopathy, and/or a protein lacking in a subject with a metabolic disorder. See, e.g., U.S. Publication Nos. 20120128635; 20140093913; 20140080216 and 20140155468.

The genomically-modified cells described herein are typically modified via nuclease-mediated (ZFN, TALEN and/or CRISPR/Cas) targeted integration to insert a sequence encoding a therapeutic protein into the genome of one or more cells of the subject (in vivo or ex vivo), such that the cells produce the protein in vivo.

In certain embodiments, the methods further comprise inducing cells of the subject, particularly liver cells, to proliferate (enter the cell cycle), for example, by partial hepatectomy and/or by administration of one or more compounds that induce hepatic cells to undergo cell cycling. Subjects include but are not limited to humans, non-human primates, veterinary animals such as cats, dogs, rabbits, rats, mice, guinea pigs, cows, pigs, horses, goats and the like.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261; and 8,586,526 see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

"TtAgo" is a prokaryotic Argonaute protein thought to be involved in gene silencing. TtAgo is derived from the bacteria *Thermus thermophiles*. See, e.g., Swarts et al, (2014) *Nature* 507(7491_:258-261: G. Sheng et al., (2013) *Proc. Natl, Acad. Sci. USA*. 111, 652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)"refers to the specialized form of such exchange that takes place, for example, during repair of double-strand breaks in cells via homology-directed repair mechanisms. This process requires nucleotide sequence homology, uses a "donor"

molecule to template repair of a "target" molecule (i.e., the one that experienced the double-strand break), and is variously known as "non-crossover gene conversion" or "short tract gene conversion,"because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger nucleases and/or TALENs can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid (donor) sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more nuclease domains or transcriptional regulatory domains such as activation or repression domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (ZFP, TALE) is fused to a cleavage domain (e.g., endonuclease domain such as FokI, meganuclease domain, etc.), the DNA-binding domain and the cleavage domain are in operative linkage if, in the fusion polypeptide, the DNA-binding domain portion is able to bind its target site and/or its binding site, while the cleavage (nuclease) domain is able to cleave DNA in the vicinity of the target site. The nuclease domain may also exhibit DNA-binding capability (e.g., a nuclease fused to a ZFP or TALE domain that also can bind to DNA). Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, CCR5, HPRT, AAVS1, Rosa and albumin. See, e.g., U.S. Pat. Nos. 7,888, 121; 7,972,854; 7,914,796; 7,951,925; 8,110,379; 8,409, 861; 8,586,526; U.S. Patent Publications 20030232410; 20050208489; 20050026157; 20060063231; 20080159996; 201000218264; 20120017290; 20110265198; 20130137104; 20130122591; 20130177983; 20130177960; and 20130122591 and U.S. application Ser. No. 14/278, 903).

Nucleases

Described herein are compositions, particularly nucleases, that are useful in integration of a donor sequence in the genome of a cell from or in a subject. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains, or megaTALs: fusions between a TALE DNA binding protein and a homing endonuclease or meganuclease) and/or a Ttago or CRISPR/Cas system utilizing an engineered single guide RNA).

A. DNA-Binding Domains

Any DNA-binding domain can be used in the compositions and methods disclosed herein, including but not limited to a zinc finger DNA-binding domain, a TALE DNA binding domain, the DNA-binding portion of a CRISPR/Cas nuclease, a Ttago nuclease, or a DNA-binding domain from a meganuclease.

The DNA-binding domain can be bind to any target sequence. In certain embodiments, the DNA-binding domain binds to an endogenous sequence, for example a safe harbor within the genome. Non-limiting examples of safe harbor loci that can be targeted by the DNA-binding domain of one or more nuclease(s) include CCR5, CCR5, HPRT, AAVS1, Rosa and albumin. See, e.g., U.S. Pat. Nos. 7,888, 121; 7,972,854; 7,914,796; 7,951,925; 8.110,379; 8,409, 861; 8,586,526; U.S. Patent Publications 20030232410; 20050208489; 20050026157; 20060063231; 20080159996;

201000218264; 20120017290; 20110265198; 20130137104; 20130122591; 20130177983, 20130177960 and 20150056705.

In certain embodiments, the nuclease is a naturally occurring or engineered (non-naturally occurring) meganuclease (homing endonuclease). Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. Engineered meganucleases are described for example in U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain. DNA-binding domains from meganucleases may also exhibit nuclease activity.

In other embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et at (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et at (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove, (2009) *Science* 326:1501 and Boch et at (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid).

Engineered TAL proteins have been linked to a FokI cleavage half domain to yield a TAL effector domain nuclease fusion (TALEN), including TALENs with atypical RVDs. See, e.g., U.S. Pat. No. 8,586,526. Thus, in some embodiments, the TALENs comprise a TAL effector DNA-binding domain and a restriction endonuclease domain (e.g., FokI).

In some instances, TAL DNA binding domains have been linked to homing endonucleases/meganucleases to make "MegaTALs". These fusion proteins rely on the low cutting frequency of meganucleases naturally in an attempt to reduce any off-site cleavage by an engineered nuclease while exploiting the TAL DNA binding domain to direct the site specific cleavage (see Boissel (2013) *Nucl Acid Res* 1-11).

In still further embodiments, the TALEN comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et at (2013) *Nat Comm:* 1-8 DOI: 10.1038/ncomms2782).

In addition, the nuclease domain of TALENs as described herein may also exhibit DNA-binding functionality and any TALENs may be used in combination with additional TALENs (e.g., one or more TALENs (cTALENs and/or FokI-TALENs) with one or more mega-TALEs.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA-binding domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some embodiments, the TALEN comprises a endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et at (2013) *Nat Comm:* 1-8 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

Selection of target sites and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some embodiments, the DNA binding domain is part of a TtAgo system (see Swarts et al, *ibid*; Sheng et al, *ibid*). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., *ibid*). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. *ibid*). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., *ibid*). Ago from *Rhodobacter sphaeroides* (RsAgo) has similar properties (Olivnikov et al. *ibid*).

Exogenous guide DNAs of arbitrary DNA sequence can be loaded onto the TtAgo protein (Swarts et al. *ibid*.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have enhanced activity at 37 degrees Celsius. Ago-RNA-mediated DNA cleavage could be used to affect a panopoly of outcomes including gene knock-out, targeted gene addition, gene correction, targeted gene deletion using techniques standard in the art for exploitation of DNA breaks.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce a Cas protein and is genetically engineered to produce a Cas protein.

Exemplary CRISPR/Cas nuclease systems targeted to safe harbor and other genes are disclosed for example, in U.S. application Ser. No. 14/278,903.

Thus, the nuclease can comprise any DNA-binding domain (e.g., zinc finger protein, TALE, single guide RNA) that specifically binds to a target site in any gene.

B. Cleavage Domains

Any suitable cleavage domain can be operatively linked to a DNA-binding domain to form a nuclease. such as a zinc finger nuclease, a TALEN, or a CRISPR/Cas nuclease system.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. No. 7,914,796, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Pat. No. 8,623,618, incorporated by reference herein)). In other embodiments, the engineered cleavage half domain comprises the "Sharkey" and/or "Sharkey'" mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. Nos. 7,888,121; 7,914,796; 8,034,598 and 8,823,618.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., U.S. Pat. Nos. 7,888,121; 8,409,861; 7,972,854; 7,914,796; 7,951,925; 7,919,313; and U.S. Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Thus, the nuclease specifically targets any site into which it is desired to insert a donor (transgene).

Target Sites

As described in detail above, DNA-binding domains can be engineered to bind to any sequence of choice, for example in a safe-harbor locus such as CCR5, HPRT, albumin, Rosa, CXCR4 and AAVS1. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

For treatment of a disorder (e.g., hemophilia, a lysosomal storage disorder, a metabolic disorder, a hemoglobinopathy) via targeted insertion of a sequence encoding a functional version of one or more proteins aberrantly expressed in a subject with the disorder, any desired site of insertion in the genome of the subject is cleaved with a nuclease, which stimulates targeted insertion of the donor polynucleotide carrying the protein-encoding sequence. DNA-binding domains of the nucleases may be targeted to any desired site in the genome. In certain embodiments, the DNA-binding domain of the nuclease is targeted to an endogenous safe harbor locus, for example an endogenous albumin locus.

Donor Sequences

Any donor sequence can be integrated using the methods described herein, including one or more DNA sequences. For treating a disorder in which a protein is aberrantly expressed (lacking and/or non-functional), the donor sequence (also called an "exogenous sequence" or "donor" or "transgene") comprises a sequence encoding a functional version of the protein, or part thereof, to result in a sequence encoding and expressing a functional protein following donor integration. Non-limiting examples of suitable proteins include clotting factor protein transgenes for treatment of hemophilias, for example, Factor VII (F7), Factor VIII (F8), Factor IX (F9 or F.IX or FIX) and/or Factor X (F10 or FX), including functional fragments of these proteins. In certain embodiments, the B-domain of the F8 protein is deleted. See, e.g., Chuah et al. (2003) Blood 101(5):1734-1743. In other embodiments, the transgene comprises a sequence encoding a functional F.IX protein, or part thereof, to result in a sequence encoding and expressing a function F.IX protein following donor integration. See, also, U.S. application Ser. No. 14/565,014.

The donor molecule may be inserted into an endogenous gene such that all, some or none of the endogenous gene is expressed. For example, a transgene comprising functional protein sequences as described herein may be inserted into an endogenous albumin locus such that some or none of the endogenous albumin is expressed with the transgene.

The donor (transgene) sequence is introduced into the cell sequentially (e.g., prior to, or subsequent to), expression of the fusion protein(s) (e.g., nucleases). The donor polynucleotide may contain sufficient homology (continuous or discontinuous regions) to a genomic sequence to support homologous recombination (or homology-directed repair) between it and the genomic sequence to which it bears homology or, alternatively, donor sequences can be integrated via non-HDR mechanisms (e.g., NHEJ donor capture), in which case the donor polynucleotide (e.g., vector) need not containing sequences that are homologous to the region of interest in cellular chromatin. See, e.g., U.S. Pat. Nos. 7,888,121 and 7,972,843 and 8,703,489 and U.S. Publication Nos. 20110281361 and 20110207221.

A donor sequence may also be used for gene correction or alteration of an endogenous gene. Such a donor may be an oligonucleotide used for correction of a mutation in an endogenous gene or may be used to alter the wild type sequence to impart an improvement in gene product characteristics. The donor may also be used to correct or alter sequences in coding sequences, regulatory sequences or other non-coding sequences.

The donor polynucleotide can be DNA or RNA, single-stranded, double-stranded or partially single- and partially double-stranded and can be introduced into a cell in linear or circular (e.g., minicircle) form. See, e.g., U.S. Pat. No. 8,703,489 and U.S. Publication Nos. 20110281361 and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus).

The donor is generally inserted so that its expression is driven by the endogenous promoter at the integration site (e.g., the endogenous albumin promoter when the donor is integrated into the patient's albumin locus). Thus, the transgene typically lacks control elements (e.g., promoter and/or enhancer) that drive its expression (e.g., also referred to as a "promoterless construct"). Nonetheless, it will be apparent that the donor may comprise a promoter and/or enhancer, for example a constitutive promoter or an inducible or tissue specific (e.g., liver- or platelet-specific) promoter that drives expression of the functional protein upon integration.

The donor sequence can be integrated specifically into any target site of choice, thereby eliminating the issues associated with random integration in traditional gene therapy.

When endogenous (e.g., albumin) sequences are expressed with the transgene, the endogenous sequences may be full-length sequences (wild-type or mutant) or partial sequences. Preferably the albumin sequences are functional. In certain embodiments, the endogenous sequences are albumin sequences that may be expressed with the transgene (either from the endogenous locus or as part of the transgene). Non-limiting examples of the function of these full length or partial albumin sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Any of the donor sequences may include one or more of the following modifications: codon optimization (e.g., to human codons) and/or addition of one or more glycosylation sites. See, e.g., McIntosh et al. (2013) *Blood* (17):3335-44.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 8,586,526; 6,453, 242; 6,503,717; 6,534,261; 6,599,692; 6,607,882; 6,689, 558; 6,824,978; 6,933,113; 6,979,539; 7,013,219; and 7,163, 824 the disclosures of all of which are incorporated by reference herein in their entireties.

Nucleases and/or donor constructs as described herein may also be delivered using vectors containing sequences encoding one or more of the zinc finger protein(s), TALEN protein(s) and/or a CRISPR/Cas system. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs. In certain embodiments, one vector is used to carry both the transgene and nuclease(s). In other embodiments, two vector are used (the same or different vector types), where one vector carries the nuclease(s) (e.g., left and right ZFNs of a ZFN pair, for example with a 2A peptide) and one carries the transgene. In still further embodiments, three vectors are used where the first vector carries one nuclease of a nuclease pair (e.g., left ZFN), the second vector carries the other nuclease of a nuclease pair (e.g., right ZFN) and the third vector carries the transgene.

The donors and/or nuclease may be used at any suitable concentrations. In certain embodiments, the donor and separate nuclease vector(s) are used the same concentration. In other embodiments, the donor and separate nuclease vector(s) are used at different concentrations, for example, 2-, 3-, 4-, 5-, 10- or more fold of one vector than other (e.g., more donor vector(s) than nuclease vector(s). When AAV vectors are used for delivery, for example, the donor- and/or nuclease-comprising viral vector(s) are between $1\times10^8$ and $1\times10^{13}$ particles per dose (e.g., cell or animal).

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Felgner, *TIBTECH* 11:211-217 (1993); Mitani & Caskey, TIBTECH 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered nucleases and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleases and/or donors include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10 or pseudotyped AAV such as AAV2/8, AAV8.2, AAV2/5 and AAV2/6 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding polynucleotides and/or donor transgene polynucleotides) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) Nature Genetics 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, the nucleases and donors can be carried by the same vector. Alternatively, a donor polynucleotide can be carried by a plasmid, while the one or more nucleases can be carried by an AAV vector. Furthermore, the different vectors can be administered by the same or different routes (intramuscular injection, tail vein injection, other intravenous injection, intraperitoneal administration and/or intramuscular injection). In the methods described herein, the vectors are administered sequentially, typically by first administering the nuclease(s) and subsequently administering the transgene. Multiple administrations of nuclease(s) and/or transgenes may be conducted.

Thus, the instant disclosure includes in vivo or ex vivo treatment of any disorder in which a protein is aberrantly expressed. Non-limiting examples of disease that can be treated include hemophilias (e.g., via nuclease-mediated integration of F7, F8, F9 and/or F10), lysosomal storage diseases, metabolic diseases, hemoglobinopathies, and other genetic diseases. See, e.g., See, e.g., U.S. Publication Nos. 20120128635; 20140093913; 20140080216 and 20140155468.

The compositions are administered to a human patient in an amount effective to obtain the desired concentration of the therapeutic polypeptide in the serum, the liver or the target cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains, TALENs (TAL-effector DNA binding domains and a restriction endonuclease or meganuclease domains), Ttago nuclease and/or a CRISPR/Cas system comprising an engineered single guide RNA.

EXAMPLES

Example 1

Optimization of the Order of Addition of ZFN-Nuclease (mRNA) and Donor-AAV in Human Primary Hepatocytes In order to identify the optimal timing of AAV Donor addition relative to transfection with mRNAs encoding ZFN in vitro, human primary hepatocytes (Celsis) were used. For all hepatocyte cultures, the following methods and conditions were used. 24 or 48-well cell culture dishes (VWR) were used which were coated with a mixture of 250 ul matrigel (BD Biosciences) in 10 ml hepatocytes basal medium, HBM (Lonza), each well was covered in 150 μl of the mixture. Plates were incubated for 1 hour at 37° C. Thawing/plating media was prepared by combining 18 ml InVitroGRO CP medium (Celsis In Vitro Technologies) and 400 ul Torpedo antibiotic mix (Celsis In Vitro Technologies). Once the plates were prepared, the cells (Celsis In Vitro Technologies, male rhesus monkey plateable hepatocytes, or female plateable human hepatocytes) were transferred from the liquid nitrogen vapor phase directly into the 37° C. water bath. The vial was stirred gently until the cells were completely thawed.

The cells were transferred directly into a 50 ml conical tube containing 5 ml of pre-warmed thawing/plating medium. To transfer cells completely, the vial was washed with 1 ml of thawing/plating medium. The cells were re-suspended by gently swirling the tube. A small aliquot (20 μl) is removed to perform a cell count and to determine cell viability using trypan blue solution, 1:5 (Cellgro). The cells were then centrifuged at 75×g for 5 minutes. The supernatant was decanted completely and the cells were resuspended at 1×10e6 cells/ml. The matrigel mixture was aspirated from the wells and cells were seeded at 2×10e5 cells/well in a 48 well dish. Cells were then incubated in 37° C./5% CO2 incubator. At the time of transduction/transfection, cells were switch to maintenance medium HCM (Lonza and HCM™ SingleQuots™).

The hepatocytes for this experiment were seeded on BD Matrigel™ (BD Biosciences) coated 24 well plates (2e5 cells per well) and left untreated for 24 hours to recover. Cells were kept in HCM™ (Lonza). 24 hours after seeding the cells were exposed to an MOI of 1e5 of AAV2/6 particles containing a DNA donor encoding the secreted embryonic alkaline phosphatase (SEAP) reporter gene protein flanked by hALB specific homology arms. In these experiments, the AAV virus was prepared using standard HEK293 production protocols (see Matsushita et at (1998) Gene Therapy 5:938-945).

Either on the same day or 24, 48 or 72 hours later, respectively, 1 μg of mRNA encoding the human albumin-specific ZFN pair 35364-ELD-2A-35396-KKR (a single mRNA encoding both nucleases of the 35364/35396 pair separated by a self-cleaving 2A peptide sequence) was transfected using Lipofectamine® RNAiMAX (Invitrogen). (See US Patent Publication 20130177983 for a description of human albumin specific ZFN pair 35364/35396).

Supernatants of the hepatocytes were harvested seven days after and measured for SEAP activity (SEAP reporter Gene Assay; Roche).

Figure 2:
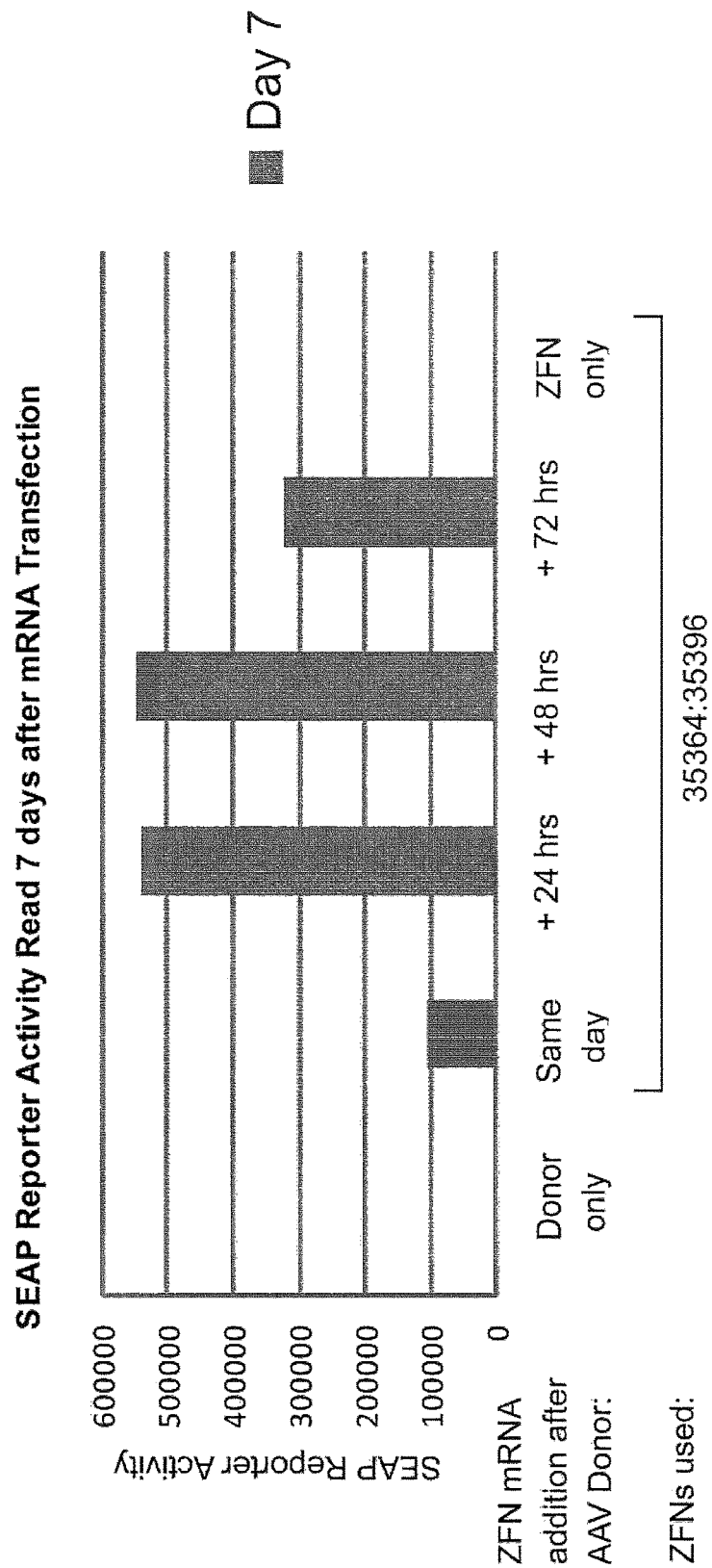
FIG. 2 is a graph depicting transgene activity following insertion in primary human hepatocytes. In this experiment, AAV2/6 virus particles comprising a DNA donor encoding the secreted embryonic alkaline phosphatase (SEAP) reporter gene protein flanked by hALB specific homology arms was introduced into the cells at a MOI of 1e5. mRNAs encoding human albumin specific-ZFNs were introduced to the cells at various time points from 0 to 72 hours following the introduction of the donor containing AAV. Transgene expression was then measured 7 days later. The graph demonstrates that introduction of the nucleases 24-48 hours after AAV-donor introduction lead to the optimum transgene expression.

The results showed that transfection of ZFN mRNA is optimal at 24 hours or 48 hours after addition of AAV donor (FIG. 2). In contrast, delivery of ZFN Donor on the same day or 72 hours apart was significantly less efficient.

Example 2

Optimization of Order of Addition of ZFN-Nuclease (mRNA) and Donor-AAV

Figure 3A:
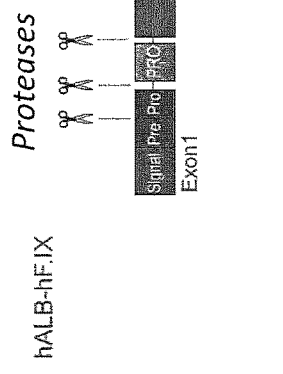
FIGS. 3A to 3C depict the results of an investigation of varying the order of addition of the nucleases and transgene donor for expression of human Factor 9 (hF.IX).
Figure 3B:
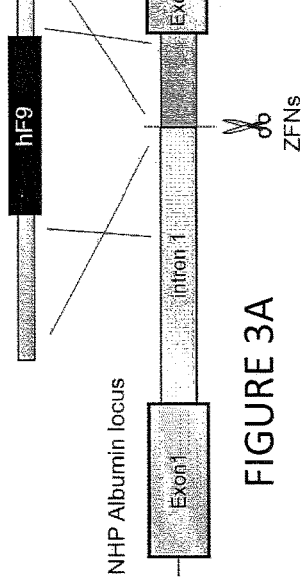
Figure 3C:
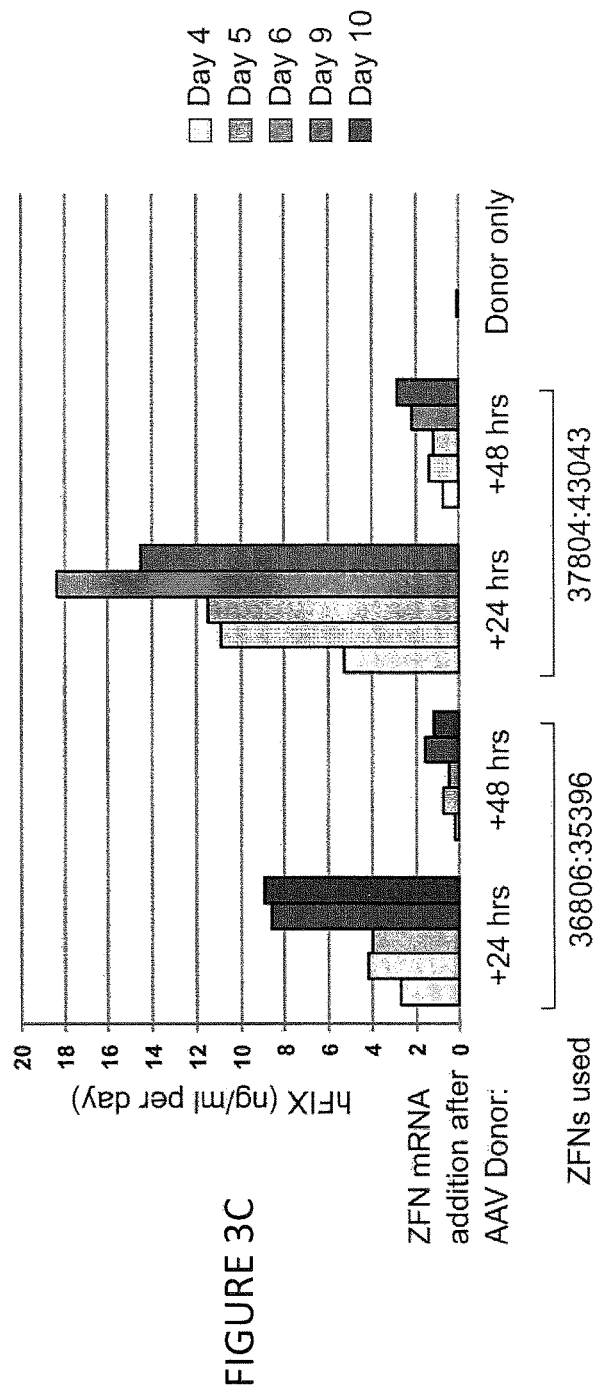

In order to test the optimized conditions from Example 1 using a more clinically relevant transgene donor, the human Factor 9 (hF9) gene was utilized as a donor and was tested in NHP (rhesus) primary hepatocytes. The hepatocytes were seeded on matrigel coated 48 well plates (2e5 cells per well) as described above and left untreated for 24 hours to recover. 24 hours after seeding the cells were exposed to an MOI of 3e5 of AAV2/6 particles containing the hF9 transgene flanked by rhesus albumin specific homology arms of 276 nucleotides (left) and 100 nucleotides (right) respectively (see FIG. 3). Either 24 or 48 hours after donor ANY delivery, two different pairs of single mRNAs (0.5 μg per single ZFN mRNA) encoding either rhesus albumin-specific ZFNs 37804-ELD/43043-KKR or 36806-FokI WT/35396-FokI WT were transfeceted as described above. (See U.S. Patent Publication 20130177983, 20150159172 and 20150166618 for a description of various albumin specific ZFN pairs). In this example, the two ZFNs were delivered as separate mRNAs, rather than as one RNA separated by, a 2A fusion peptide as described in Example 1.

Supernatants of the hepatocytes were harvested every day, and those from days 4 to 10 (mRNA transfection is day 1) were analyzed by ELISA against the human F.IX protein using a primary antibody (Hematologic systems), which can distinguish between rhesus F.IX protein and human F.IX. The results showed that transfection of ZFN mRNA 24 hours after addition of the AAV carrying the trangene donor was optimal for transgene expression (see FIG. 3C).

Figure 4:
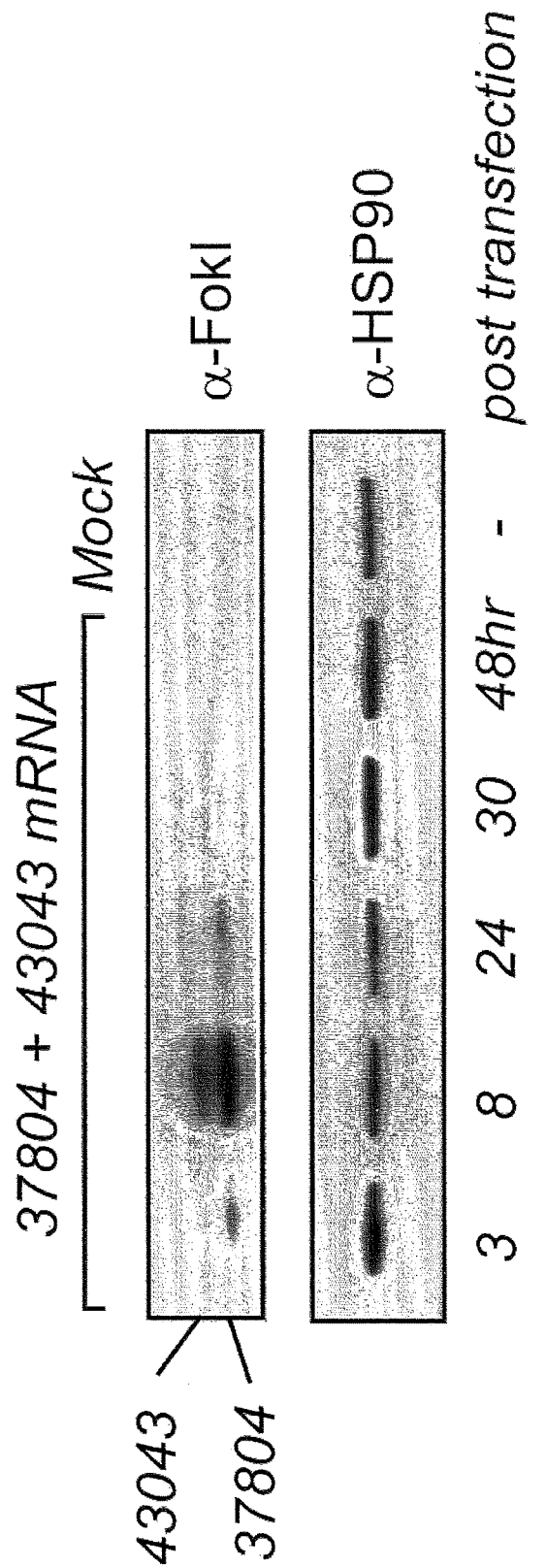
FIG. 4 is a Western blot depicting the expression of one of the two NHP (Rhesus) Albumin specific ZFN proteins following mRNA introduction in NHP (rhesus) primary hepatocytes. For detection of ZFNs an anti-FokI antibody was used while HSP90 served as loading control. The data shows that ZFN protein levels peak approximately 8 hours post transfection and is nearly undetectable 48 hours post transfection.

These results are consistent with the observed ZFN expression profile in NHP hepatocytes which peaked between 9-24 hours after ZFN-encoding mRNA transfection using the 37804/43043 pair as detected by Western analysis (FIG. 4). ZFN expression was monitored through standard Western blot protocols, using an anti-Fok I primary antibody.

Example 3

Optimization of ZFN-Nuclease (AAV2/6) and hF9-Donor (AAV2/6) Addition in NHP Hepatocytes An in vitro AAV transduction system where both ZFN and donor were delivered to the cells using AAV2/6 viral vectors was investigated to see if delayed addition of ZFN-AAV and donor-AAV is also superior to same day addition. Both ZFN and Donors were delivered to NHP (rhesus) primary hepatocytes, where the cells were prepared as described above, and the AAV2/6 (either the ZFN-AAV or the donor-AAV) was introduced to the cells by adding viral stock pre-diluted in medium. The virus was kept on the cells for 24 hours and then hepatocyte medium was exchanged. Further, supernatants were harvested daily and tested for hF.IX secretion by ELISA using a primary antibody (Hematologic systems) which can distinguish between rhesus F.IX protein and human F.IX.

For these experiments, NHP (rhesus) primary hepatocytes were transduced with AAV2/6 viruses containing one of the two primate albumin-specific ZFNs 36806 or 35396 and AAV2/6 virus comprising the donor (the hF9 transgene with primate albumin homology arms). The two virus types were either introduced on the same day or the ZFN-AAV was delivered first and then the donor-AAV was delivered 7, 24 or 48 hours later. The ratio of donor-AAV to ZFN-AAV was 5:1 with resulting multiplicities of infection (MOIs) of 3e5 per single ZFN-AAV (total ZFN MOI: 6e5) and 3e6 for the donor-AAV.

Figure 5A:
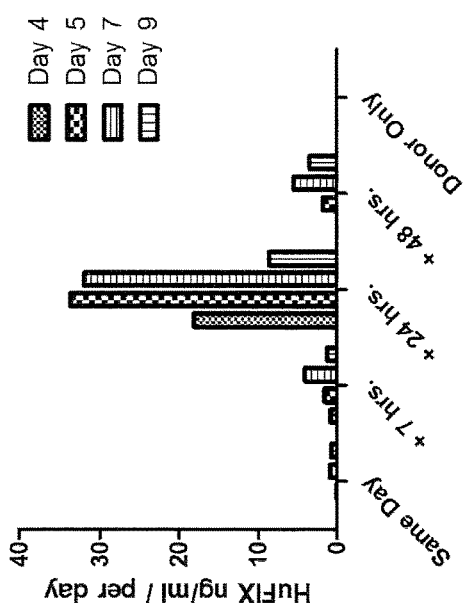
FIGS. 5A and 5B depict nuclease-mediated targeted integration of a transgene in vitro in rhesus primary hepatocytes via sequential administration of nuclease and transgene where both the ZFNs and donor are delivered as viral vectors. Both the ZFN (specific for the rhesus albumin gene) and hF9 donor were delivered via recombinant AAV2/6 virus, and the donor hF9 transgene was flanked with homology arms containing sequences homologous to those surrounding the cleavage site in the rhesus albumin gene. The ZFN containing virus was added first, and then the donor comprising virus was added either on the same day or up to 48 hours later.

The results showed that the hF.IX expression detected in the cell supernatant during all time points collected was highest when the donor-AAV was delivered 24 hr after the ZFN-AAV (see FIG. 5A).

Figure 5B:
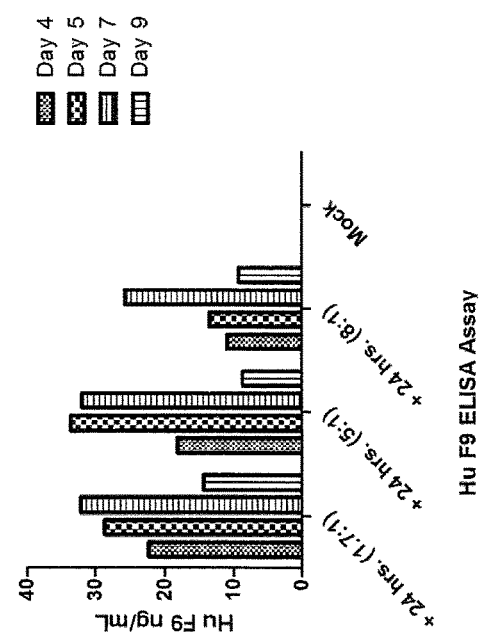

The ratios of the donor-AAV and the ZFN-AAV were then varied and delivered as before at either the same time, the donor-AAV was delivered at 7, 24 or 48 hours following the ZFN-AAV. Similar to the previous result, delivery of the AAV-donor 24 hours after the ZFN-AAV gave successful transgene expression (see FIG. 5B) in this experiment.

Example 4

Optimization of ZFN-Nuclease (AAV2/6) and hF9-Donor (AAV2/6) Addition in NHP Hepatocytes Via End-capture In Example 3, the hF9 transgene was flanked by homology arms with homology to region surrounding the ZFN cleavage site in the rhesus albumin gene, allowing the transgene to be integrated either via homology directed pair or by NHEJ-dependent end capture. A donor was then designed with homology arms that are not homologous to the rhesus albumin gene (the homology arms are homologous to the human F9 gene). Integration of this donor then would be required to occur through NHEJ-dependent end capture only.

Figure 6:
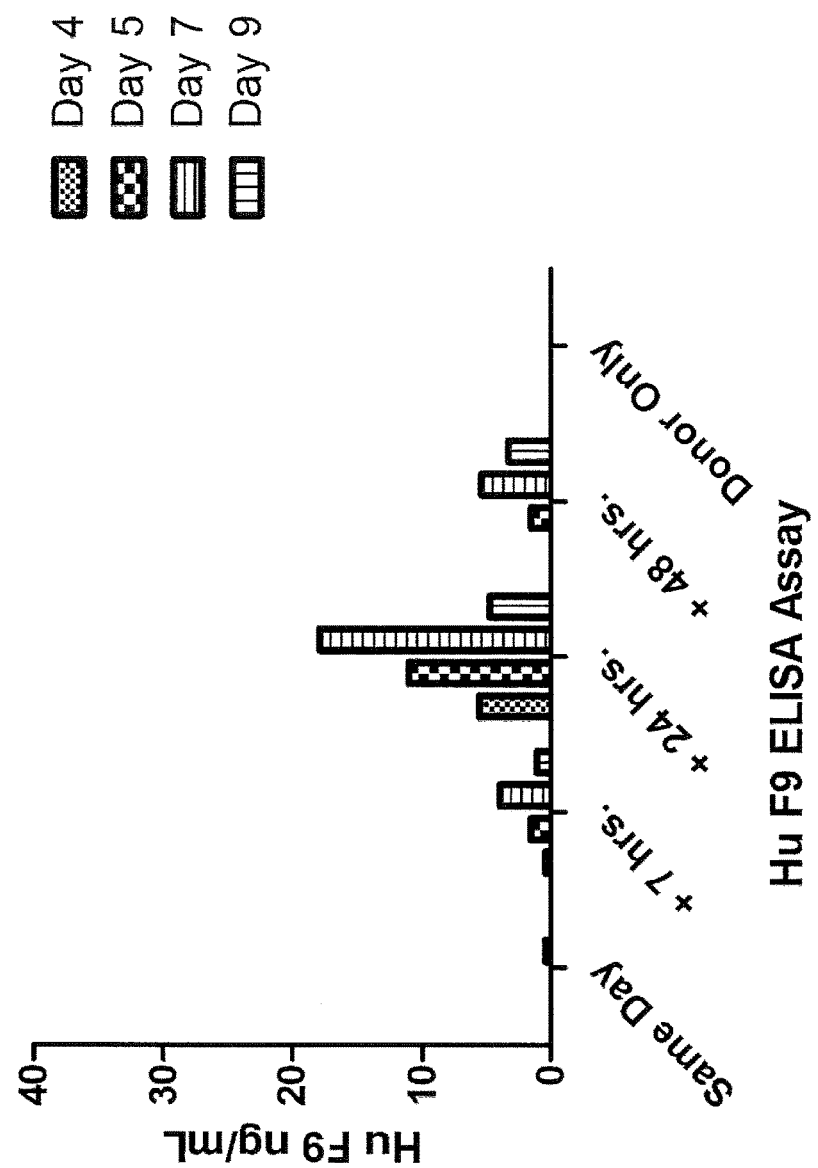
FIG. 6 is a graph depicting hF.IX transgene expression when the hF9 transgene was flanked with regions of homology to the human F9 gene, rather than homology arms that are homologous to the NHP albumin locus where the transgene was being inserted, a scheme that forces integration of the donor only through NHEJ-dependent end capture. In this case, delay of the donor-AAV addition for 24 hours following ZFN-AAV treatment was still optimum for hF.IX expression.

Experimental conditions were those described in Example 3 where the ZFN-AAV were added and then the donor-AAV was added either immediately or 7, 24 or 48 hours later. Similar to above, cell supernatant was collected and analyzed for hF.IX protein expression. The results (see FIG. 6) demonstrated that the delay of 24 hours prior to donor AAV transfection was optimal for maximal transgene expression independently of the integration mechanism.

Example 5

Optimization of ZFN-Nuclease (AAV2/6) and hF9-donor (AAV2/6) Addition in NHP Hepatocytes Based on the results from the previous examples, it appears that increased transgene (e.g., hF.IX) expression is tightly linked to nuclease (ZFN) expression and activity. Therefore the optimized conditions of ZFN delivery first and then delivery of the donor containing AAV 24 hours later may have led to increased ZFN activity in the absence of the donor AAV for the first 24 hours, which then drives increased donor integration/transgene expression (hF.IX secretion).

To test this, NHP (rhesus) primary hepatocytes were treated with a rhesus albumin-specific ZFN pair (37804: 43043) and a hF9 transgene donor flanked by homology arms that are homologous to the human albumin locus, meaning that integration of the hF9 transgene can only occur through NHEJ-dependent end capture. Different Donor: ZFN1:ZFN2 ratios, (2:1:1, 6:1:1 and 10:1:1) were also examined to observe the impact of ZFN:Donor ratio on both ZFN activity and Donor integration. In these experiments the MOI of AAV2/6 encoding the ZFN was fixed at 3e5 per single ZFN (total ZFN MOI: 6e5) and therefore the AAV2/6 Donor MOIs for the other conditions were 6e5 (2:1:1), 1.8e6 (6:1:1) and 3e6 (10:1:1), respectively.

NHP (rhesus) primary hepatocytes (Celsis) were seeded as described above, and both ZFN and donor comprising AAV were delivered as described above.

The experiment was carried out in two plates in parallel. The first plate was harvested four days after ZFN addition to extract genomic DNA (using Qiagen QIAamp DNA micro kit) and analyzed for ZFN activity as follows. Briefly, the region comprising the cleavage site was amplified by PCR, and following amplification, the PCR product was sequenced via MiSeq high throughput sequencing analysis according to manufacturer's instructions (Ilumina).

For the second plate, duplicate experimental conditions as those used for the first plate were used and supernatants were collected at three time points: 2 days after ZFN addition, 5 days after ZFN addition (where the supernatants from days 3-5 were combined) and 8 days after ZFN addition (where the supernatants from days 6-8 were combined). These supernatants then were tested for secreted hF.IX protein using a primary antibody (Hematologic systems) which can distinguish between rhesus F.IX protein and human F.IX protein. Additionally, cells were harvested at Day 8 to extract genomic DNA for ZFN activity analysis by sequencing as described above.

Figure 7A:
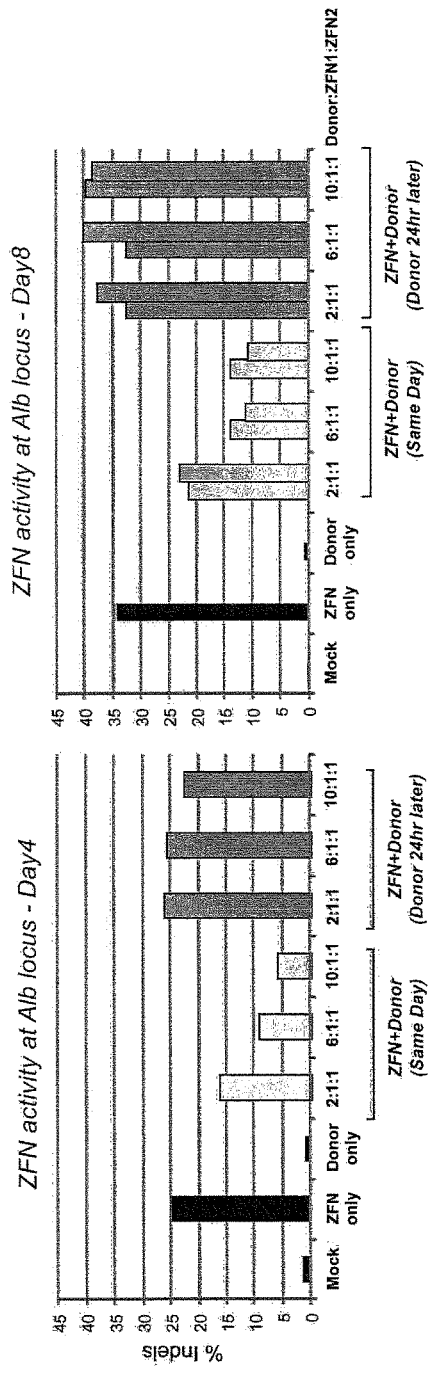
FIGS. 7A and 7B depict the results of delayed hF9 transgene AAV-donor viral introduction where the hF9 transgene is flanked with homology arms for the human albumin locus, not the NHP albumin locus, forcing integration of the trangene through NHEJ-dependent end capture.
Figure 7B:
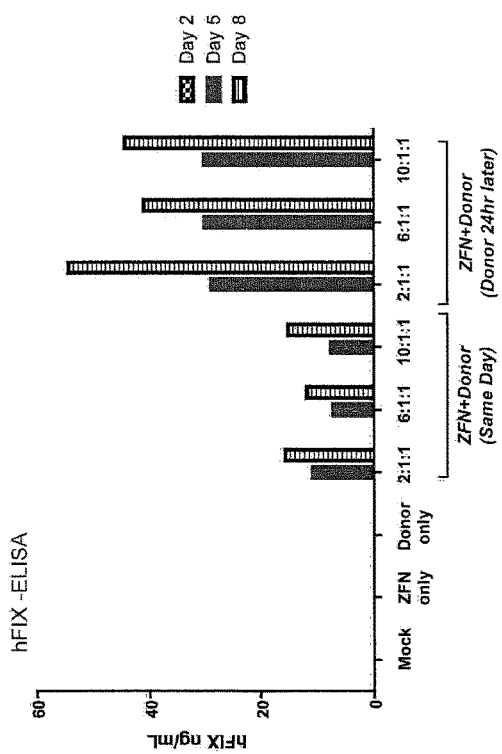

The results showed that same day transduction of AAV-ZFN and AAV-donor lead to decreased ZFN activity compared to transduction with ZFN alone. The sequencing analysis detected less indels on days 4 and 8 in all ZFN: donor ratios in the samples where the ZFN and donor-AAV particles were transduced on the same day (see FIG. 7). In contrast, when the AAV-ZFN was added first followed by the AAV-donor 24 hours later, the ZFN activity (% indels) was identical with the ZFN only transfection sample, irrespective of the ZFN:Donor ratio.

As expected the ZFN activity also correlated with hF.IX protein secretion, indicative of hF9 transgene integration, as detected by ELISA. As before optimized delivery conditions lead to a more than 2 fold increase of hF.IX secretion irrespective of the ZFN:Donor ratio.

Example 6

In Vivo Testing of Staggered ZFN-Nuclease (AAV2/8) and hF9-donor (AAV2/8) Addition in Mice In order to test whether the optimized AAV-ZFN/AAV-donor addition conditions can also be used in vivo, several addition strategies were tested side-by-side in mice using the mouse albumin-specific ZFNs 30725:30724 and a hF9 transgene donor that was flanked with homology arms with homology to the mouse albumin gene surrounding the ZFN cleavage site (ZFNs 30724 and 20725 as described in U.S. Patent Publication 20130177983 with engineered cleavage domains).

C57/Bl6 mice (cohorts of five) were injected with AAV2/8 encoding either 1.5 e11 (total) viral genomes (VGs) of AAV-ZFN only, or 9e11 (total) AAV-donor plus AAV-ZFN, which represents a Donor: ZFN ratio of 3:1. For this study either the donor-AAV was delivered first and then the ZFN-AAV was delivered 24 hours later (group 1); both ZFN-AAV and donor-AAV were administered at the same time (group 2); ZFN-AAV was delivered first and then the donor-AAV was delivered 24 hours later, (group 3); or ZFN-AAV was delivered first, and the donor-AAV was delivered 72 hr later (group 4); or ZFN-AAV was delivered first, and the donor-AAV was delivered 120 hours later (group 5). In these studies, both were delivered by injection to the tail vein as described in U.S. Patent Publication No. 20120128635. Seven days after ZFN delivery in all groups, serial bleed of the different groups was carried out for analysis of hF.IX secretion into the plasma.

ELISA for human hF.IX (Affinity) performed on day seven revealed that addition of donor-AAV first was indistinguishable from addition of ZFN-AAV and donor-AAV on the same day (see FIG. 8). In contrast, if the donor-AAV was administered 24 hours or 72 hours after the ZFN-AAV, levels of hF.IX in the plasma were two to three fold higher respectively than the administration on the same day. In contrast, administration of the Donor 120 hours after the ZFN resulted in complete lack of hF9 expression. Probability analysis (Student's T test) demonstrated a significant difference between samples from the mice that got the donor and ZFN on the same day, or got the donor 24 hours ahead of time as compared to mice that got the donor-AAV three days after they had received the ZFN-AAV.

Figure 9A:
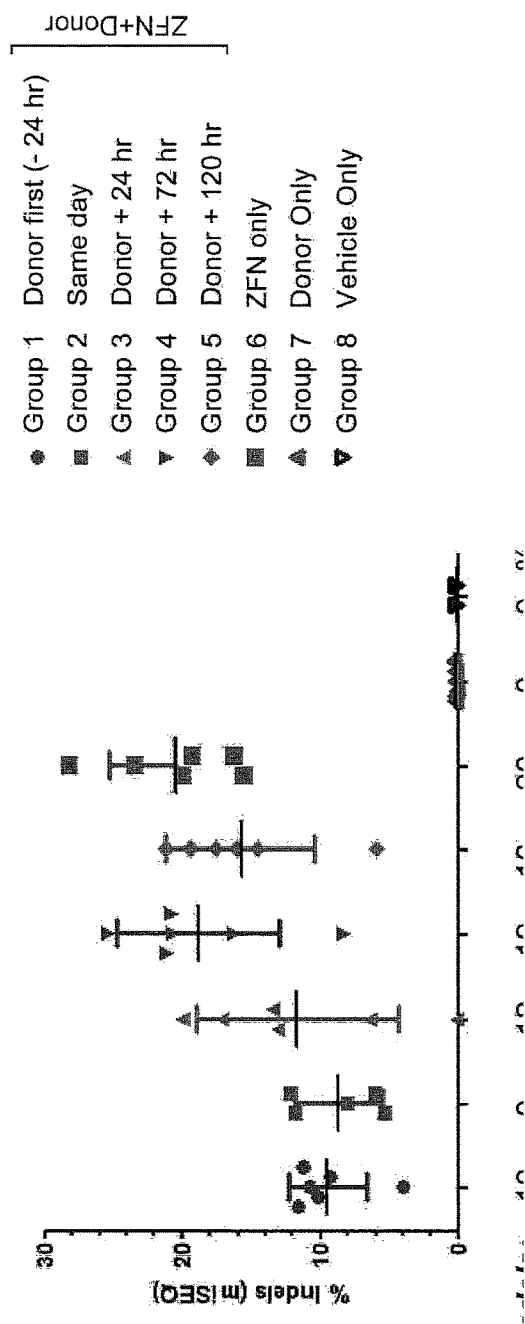
FIGS. 9A and 9B depict ZFN activity and expression in the same experiment described above.
Figure 9B:
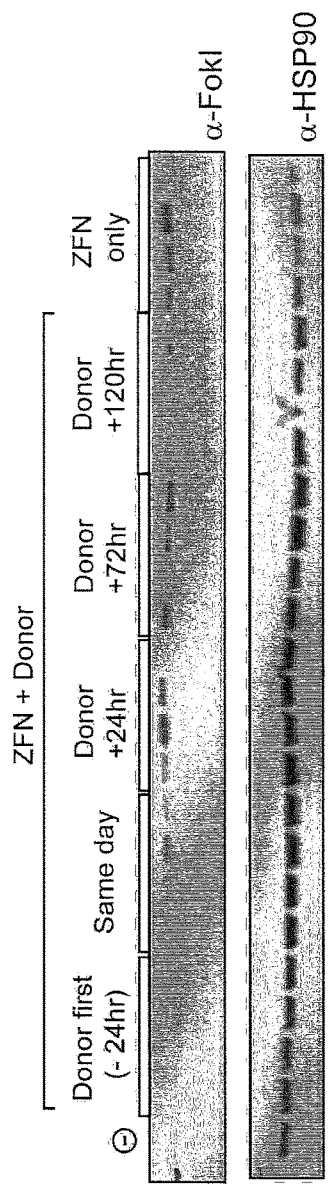

Analysis of genomic DNA from liver tissue from a satellite mouse group also sacrificed on day seven showed that the higher hF.IX expression correlated with the higher levels of albumin gene modification, which was two-fold higher when the donor-AAV was administered 3 days after the ZFN-AAV (see FIG. 9A). Additionally, the levels of targeted gene modification observed for the mice that had received the donor-AAV 3 days following the ZFN-AAV were similar to the group that only received ZFN-AAV. This was consistent with the in vitro results shown in Example 5. However, transduction efficiency (assayed by detection of VGs per diploid genome) with ZFN-AAV was the same for all groups but ZFN expression levels, as analyzed by standard Western blot analysis, were higher when either the ZFN-AAV was delivered alone or when the donor-AAV was delivered three days after the ZFN-AAV (FIG. 9B) in comparison to when the donor-AAV was given prior to, or at the same time as the ZFN-AAV.

When the different dosing cohorts are analyzed for serum hF.IX levels over time, long term expression of the transgene is observed (FIG. 10). Transgene expression can be detected even at 77 days after transduction with the AAV-ZFN. The groups all achieve appreciable transgene expression, but transduction of the AAV-ZFN three days before addition of the AAV-donor virus achieves increased expression the fastest.

Example 7

In Vivo Testing of Staggered ZFN-Nuclease (AAV2/8) and hF9-Donor (AAV2/8.2) Addition in NHP In order to test whether the optimized AAV ZFN/AAV Donor addition conditions can also be used in NHP in vivo, studies are performed using several different addition strategies in rhesus monkeys using the rhesus albumin-specific ZFNs 37804:43043 and a hF9 transgene donor that is flanked with homology arms with homology to the rhesus albumin gene surrounding the ZFN cleavage site. In these experiments, the ZFN-AAV each contain a single ZFN coding sequence, so to deliver the ZFN pair, two ZFN-AAV particle types are given. The ZFN-AAV virus particles together are given in a 8:1:1 ratio (Donor:ZFN1:ZFN2) with the AAV-donor particles, and pairs of monkeys are given the ZFN-AAV and donor-AAV either on the same day, or given ZFN-AAV 1 day or 3 days prior to the donor-AAV. Serial bleeds are performed over time to test for serum hF.IX.

Figure 11B:
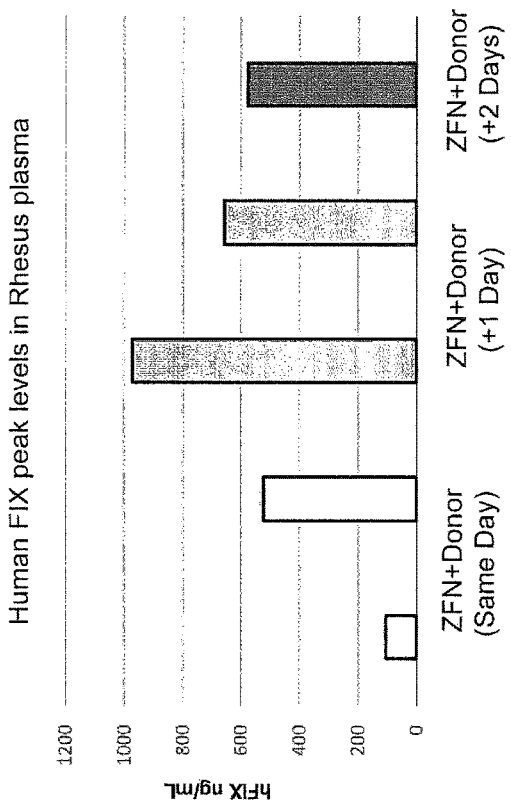
FIGS. 11A and 11B show hF.IX levels in treated animals.
Figure 11A:
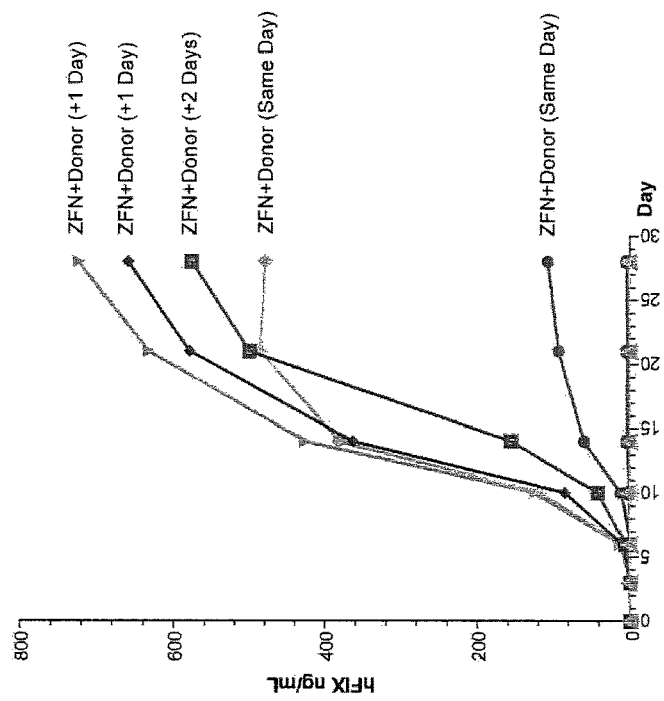

The results demonstrated that delay of 1 to 3 days between when the animals receive the ZFN-AAV and the donor-AAV gave the most rapid expression of the transgene up until Day 28 (FIG. 11A). Analysis of the hF.IX peak levels of all animals during study duration (>30 weeks) revealed that of the 5 animals expressing detectable levels of h.FIX the 3 highest expressing animals had been treated with AAV-donor particles either 1 or 2 days after the AAV-ZFN particles (FIG. 11B).

Taken together, these data show that separate administration of nucleases and donor transgenes showed significant enhancement of transgene expression (3-fold as compared to same day administration). Thus, nuclease mediated integration of transgenes can be enhanced by serial administration of nuclease(s) and transgenes when both are delivered as viral particles or mRNA, with a delay of hours to days between the administrations.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed:

1. A method for treating a Factor IX (F.IX) deficiency in a mammal, the method comprising:
   (i) intravenously administering one or more adeno-associated viral (AAV) vectors encoding a pair of zinc finger nucleases (ZFNs) or a pair of TAL-effector protein nucleases (TALENs) into a mammal with a F.IX deficiency such that a double-stranded break in an endogenous albumin gene occurs in liver cells of the mammal, and
   (ii) intravenously administering one or more AAV vectors comprising a donor sequence comprising a transgene encoding a functional F.IX protein into the mammal 1 to 3 days after administering the one or more AAV vectors encoding the pair of ZFNs or TALENs, wherein the transgene is flanked by nucleic acid sequences homologous to the albumin gene, such that the transgene is integrated into the endogenous albumin gene, the functional F.IX protein is expressed in liver cells of the mammal at increased levels as compared to mammals in which the AAV vectors of (i) and (ii) are administered on the same day.

2. The method of claim 1, wherein expression of the transgene is driven by an endogenous albumin promoter.

3. The method of claim 1, wherein the F.IX protein is a is human F.IX (hF .IX) protein.

* * * * *